United States Patent
D'Amore et al.

(10) Patent No.: US 11,680,266 B2
(45) Date of Patent: *Jun. 20, 2023

(54) ENDOMUCIN INHIBITOR AS AN ANTI-ANGIOGENIC AGENT

(71) Applicant: The Schepens Eye Research Institute, Inc., Boston, MA (US)

(72) Inventors: Patricia A. D'Amore, Newton, MA (US); Magali Saint-Geniez, Somerville, MA (US); Cindy Park-Windhol, Newton, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/110,248

(22) Filed: Dec. 2, 2020

(65) Prior Publication Data

US 2021/0163955 A1    Jun. 3, 2021

Related U.S. Application Data

(62) Division of application No. 16/089,990, filed as application No. PCT/US2017/025468 on Mar. 31, 2017, now Pat. No. 10,883,108.

(60) Provisional application No. 62/316,481, filed on Mar. 31, 2016.

(51) Int. Cl.
```
C12N 15/113   (2010.01)
A61K 31/713   (2006.01)
A61P 27/02    (2006.01)
A61P 9/00     (2006.01)
```

(52) U.S. Cl.
CPC ........ *C12N 15/1138* (2013.01); *A61K 31/713* (2013.01); *A61P 9/00* (2018.01); *A61P 27/02* (2018.01); *C12N 2310/14* (2013.01)

(58) Field of Classification Search
CPC . A61P 9/00; C12N 2310/14; C12N 2310/531; C12N 15/1138; A61K 31/713
See application file for complete search history.

(56) References Cited

U.S. PATENT DOCUMENTS

| | | | |
|---|---|---|---|
| 4,309,404 A | 1/1982 | Deneale et al. |
| 4,309,406 A | 1/1982 | Guley et al. |
| 4,521,210 A | 6/1985 | Wong |
| 4,556,552 A | 12/1985 | Porter et al. |
| 4,704,295 A | 11/1987 | Porter et al. |
| 4,816,567 A | 3/1989 | Cabilly et al. |
| 4,853,224 A | 8/1989 | Wong |

(Continued)

FOREIGN PATENT DOCUMENTS

| | | |
|---|---|---|
| EP | 0404097 A2 | 12/1990 |
| WO | 9311161 A1 | 6/1993 |

(Continued)

OTHER PUBLICATIONS

Park-Windhol et al. (Scientific Reports, 2017 vol. 7: 17138, pp. 1-13).*

(Continued)

*Primary Examiner* — Terra C Gibbs
(74) *Attorney, Agent, or Firm* — Fish & Richardson P.C.

(57) ABSTRACT

A method for reducing neovascularization in an ocular tissue is carried out by contacting the tissue with an inhibitor of endomucin expression or activity.

18 Claims, 14 Drawing Sheets

Specification includes a Sequence Listing.

(56) References Cited

U.S. PATENT DOCUMENTS

| | | |
|---|---|---|
| 4,997,652 A | 3/1991 | Wong |
| 5,164,188 A | 11/1992 | Wong |
| 5,443,505 A | 8/1995 | Wong et al. |
| 5,501,856 A | 3/1996 | Ohtori et al. |
| 5,545,806 A | 8/1996 | Lonberg et al. |
| 5,545,807 A | 8/1996 | Surani et al. |
| 5,569,825 A | 10/1996 | Lonberg et al. |
| 5,580,737 A | 12/1996 | Polisky et al. |
| 5,625,126 A | 4/1997 | Lonberg et al. |
| 5,633,425 A | 5/1997 | Lonberg et al. |
| 5,641,750 A | 6/1997 | Louis |
| 5,660,985 A | 8/1997 | Pieken et al. |
| 5,661,016 A | 8/1997 | Lonberg et al. |
| 5,731,005 A | 3/1998 | Ottoboni et al. |
| 5,766,242 A | 6/1998 | Wong et al. |
| 5,824,072 A | 10/1998 | Wong |
| 5,837,226 A | 11/1998 | Jungherr et al. |
| 5,869,079 A | 2/1999 | Wong et al. |
| 6,074,661 A | 6/2000 | Olejnik et al. |
| 6,331,313 B1 | 12/2001 | Wong et al. |
| 6,369,116 B1 | 4/2002 | Wong et al. |
| 6,573,099 B2 | 6/2003 | Graham |
| 6,699,493 B2 | 3/2004 | Wong |
| 6,719,971 B1 | 4/2004 | Carter et al. |
| 7,354,574 B2 | 4/2008 | Peyman |
| 8,293,210 B2 | 10/2012 | Huang et al. |
| 9,133,269 B2 | 9/2015 | Mcconnell et al. |
| 2002/0160393 A1 | 10/2002 | Symonds et al. |
| 2003/0027783 A1 | 2/2003 | Zernicka-goetz et al. |
| 2006/0034834 A1 | 2/2006 | Marasco et al. |
| 2008/0131484 A1 | 6/2008 | Robinson et al. |
| 2010/0222401 A1 | 9/2010 | London et al. |
| 2011/0293727 A1 | 12/2011 | De et al. |
| 2014/0031414 A1 | 1/2014 | Smith et al. |
| 2015/0018267 A1 | 1/2015 | D'amore et al. |
| 2019/0112610 A1 | 4/2019 | D'amore et al. |

FOREIGN PATENT DOCUMENTS

| | | |
|---|---|---|
| WO | 9907409 A1 | 2/1999 |
| WO | 9932619 A1 | 7/1999 |
| WO | 0001846 A2 | 1/2000 |
| WO | 0044895 A1 | 8/2000 |
| WO | 0044914 A1 | 8/2000 |
| WO | 0111086 A2 | 2/2001 |
| WO | 0129058 A1 | 4/2001 |
| WO | 0136646 A1 | 5/2001 |
| WO | 2010042749 A2 | 4/2010 |
| WO | 2017173327 A1 | 10/2017 |

OTHER PUBLICATIONS

Volz et al. (European J of Pharmaceutics and Biopharmaceutics, 2015 vol. 95:158-172).*

Jin et al. (Journal of Pharmaceutical Investigation (2017) vol. 47:373-382).*

Gadkar et al. (Biochemistry and Molecular Biology, 2015 vol. 56:5390-5400).*

Age-Related Macular Degeneration, U.S. National Library of Medicine Genetics, 8 pages.

International Search Report issued in International Application No. PCT /US2017/025468, dated Jun. 30, 2017, 6 pages.

"Retinal Vein Occlusion", U.S. National Library of Medicine, available at: https://medlineplus.gov/ency/article/007330.htm, retrieved on 2122/2018, 4 pages.

(Jun. 2014) "Retinopathy of Prematurity", American Association for Pediatric Ophthalmology and Strabismus, available at https://nei.nih.gov/health/rop/rop, 3 pages.

AOA,"Diabetic Retinopathy", American Optometric Association, available at: https://www.aoa.org/patients-and-public/eye-and-vision-problems/glossary-of-eye-and-vision-conditions/diabetic-retinopathy, 05 pages.

Bass Brenda L. (Jun. 2001) "RNA interference. The short answer", Nature, 411(6836):428-429.

Boerner et al. (Jul. 1, 1991) "Production of Antigen-Specific Human Monoclonal Antibodies from in Vitro-Primed Human Splenocytes", Journal of Immunology, 147(1):86-95.

Boyd Kierstan (2013) "Diabetic Retinopathy Diagnosis", American Academy of Ophthamology, Available from https://www.aao.org/eye-health/diseases/diabetic-retinopathy-diagnosis, 06 pages.

Chen et al. (1998) "Intracellular Antibodies as a New Class of Therapeutic Molecules for Gene Therapy", Human Gene Therapy, 5(5):595-601.

Chothia et al. (Aug. 20, 1987) "Canonical Structures for the Hypervariable Regions of Immunoglobulins", Journal of Molecular Biology, 196(4):901-917.

Chothia et al. (Dec. 28, 1989) "Conformations of immunoglobulin Hypervariable Regions", Nature, 342:877-883.

Cleveland Clinic,"Retinal Vein Occlusion", https://my.clevelandclinic.org/services/cole-eye/diseasesconditions/hic-retinal-vein-occlusion, 2015.

Elbashir et al. (May 24, 2001) "Duplexes of 21-Nucleotides RNAs Mediate RNA Interference in Cultured Mammalian Cells", Nature, 411:494-498.

Fishwild et al. (Aug. 1996) "High-Avidity Human IgG Kappa Monoclonal Antibodies from a Novel Strain of Minilocus Transgenic Mice", Nature Biotechnology, 14(7):845-851.

Genbank (Nov. 22, 2018) "Endomucin isoform 1 precursor [*Homo sapiens*]", NCBI Reference Sequence NP_057326.2, 03 pages.

Genbank (Jun. 24, 2018) "endomucin isoform 2 precursor [*Homo sapiens*]", NCBI Reference Sequence NP_001153166.1, 02 pages.

Genbank (Nov. 22, 2018) "*Homo sapiens* endomucin (EMCN), transcript variant 1, mRNA", NCBI Reference Sequence NM_016242.4, 04 pages.

Genbank (Jun. 24, 2018) "*Homo sapiens* endomucin (EMCN), transcript variant 2, mRNA", NCBI Reference Sequence NM_001159694.1, 04 pages.

Goding Jamesw. (1986) "Monoclonal Antibodies: Principles and Practice", Academic Press, 59-103.

Grossniklaus et al. (Nov. 2010) "Animal Models of Choroidal and Retinal Neovascularization", Progress in Retinal and Eye Research, 29(6):500-519.

Holliger et al. (Jul. 1993) "Diabodies": Small Bivalent and Bispecific Antibody Fragments, Proceedings of the National Academy of Sciences, 90(14):6444-6448.

Hoogenboom et al. (Sep. 20, 1992) "By-Passing immunisation: Human Antibodies from Synthetic Repertoires of Germline VH Gene Segments Rearranged in Vitro", Journal of Molecular Biology, 227(2):381-388.

Jones et al. (May 29, 1986) "Replacing the Complementarity-Determining Regions in a Human Antibody with those from a Mouse", Nature, 321(6069):522-525.

Kanki et al. (2011) "Epigenetically coordinated GATA2 binding is necessary for endothelium-specific endomucin expression", The EMBO Journal, 30(13):2582-2595.

Khetrapal Afsaneh (Dec. 2016) "Signs and Risk Factors for Eye Disease", New Medical Life Sciences, 14 pages.

Kohler et al. (1975) "Continuous Cultures of Fused Cells Secreting Antibody of Predefined Specificity", Nature, 256(5517):495-497.

Lonberg et al. (Apr. 28, 1994) "Antigen-Specific Human Antibodies from Mice Comprising Four Distinct Genetic Modifications", Nature, 368:856-859.

Lonberg et al. (1995) "Human Antibodies from Transgenic Mice", International Reviews of Immunology, 13(1):65-93.

Ludwig Annick (Nov. 3, 2005) "The Use of Mucoadhesive Polymers in Ocular Drug Delivery", Advanced Drug Delivery Reviews, 57(11):1595-1639.

Marks et al. (Jul. 1992) "By-Passing Immunization: Building High Affinity Human Antibodies by Chain Shuffling", Bio/Technology, 10(7):779-783.

Marks et al. (Dec. 5, 1991) "By-Passing Immunization: Human Antibodies from V-Gene Libraries Displayed on Phage", Journal of Molecular Biology, 222(3):581-597.

(56) References Cited

OTHER PUBLICATIONS

Marx et al. (Nov. 2013) "Incidence Rates of Spontaneous Disease in Laboratory Mice Used at a Large Biomedical Research Institution", Journal of the American Association for Laboratory Animal Science, 52(6):782-791.
Mayo Clinic (2015) "Diabetic Retinopathy, Tests and Diagnosis".
Mayo Clinic (2015) "Dry Macular Degeneration", https://www.mayoclinic.org/diseasesconditions/drymaculardegeneration/diagnosis-treatment/drc-20350381, 5 pages.
Mayo Clinic (2015) "Wet Macular Degeneration", 6 pages.
Morrison Sherie L. (Apr. 28, 1994) "Immunology. Success in Specification", Nature, 368:812-813.
National Eye Institute,"Facts About Retinopathy of Prematurity (ROP)", 3 pages.
Neuberger M. (Jul. 1996) "Generating High-Avidity Human Mabs in Mice", Nature Biotechnology, 4(7):1 page.
Park-Windhol et al. (Jun. 2015) "Endomucin Plays a Role in Developmental Retinal Vascularization and in VEGF-Induced Endothelial Cell Migration, Growth, and Morphogenesis In Vitro", Investigative Ophthalmology & Visual Science, 56(7):3404.
Park-Windhol et al. (2015) "Endomucin Plays a Role in Retinal Vascular Development and in VEGF-Induced Endothelial Cell Migration, Growth, and Morphogenesis", The FASEB Journal, 29(Suppl 1):418.
Pluckthun A. (1994) "Antibodies from *Escherichia coli*", The Pharmacology of Monoclonal Antibodies, 113:269-315.
Presta Leonard G. (1992) "Antibody Engineering", Current Opinion in Structural Biology, 2(4):593-596.
Riechmann et al. (Mar. 24, 1988) "Reshaping Human Antibodies for Therapy", Nature, 332(6162):323-327.
Seo et al. (Jun. 1999) "Dramatic Inhibition of Retinal and Choroidal Neovascularization by Oral Administration of a Kinase Inhibitor", The American Journal of Pathology, 154(6):1743-1753.
Shaki-Loewenstein et al. (Aug. 2005) "A universal strategy for stable intracellular antibodies", Journal of Immunological Methods, 303(1-2):19-39.
Smith et al. (Jan. 1994) "Oxygen-Induced Retinopathy in the Mouse", Investigative Ophthalmology & Visual Science, 35(1):101-111.
Tuschl et al. (Jun. 2002) "Small interfering RNAs: a revolutionary tool for the analysis of gene function and gene therapy", Molecular Interventions, 2(3):158-167.
Verhoeyen et al. (Mar. 25, 1988) "Reshaping Human Antibodies: Grafting an Antilysozyme Activity", Science, 239(4847):1534-1536.
Zapata et al. (Oct. 1995) "Engineering Linear F(ab')2 Fragments for Efficient Production in *Escherichia coli* and Enhanced Antiproliferative Activity", Protein Engineering, 8(10):1057-1062.
Dela Paz and D'Amore, "Arterial versus venous endothelial cells," Cell and tissue research, Jan. 2009, 335(1):5-16, 12 pages.
Geudens and Gerhardt, "Coordinating cell behaviour during blood vessel formation," Development, Nov. 2011, 138(21):4569-83.
International Preliminary Report on Patentability in International Appln. No. PCT/US2017/025468, dated Oct. 11, 2018, 5 pages.
Liu et al., "Human endomucin is an endothelial marker," Biochemical and biophysical research communications, 2001, 288:129-36.
Ng et al., "Identification of genes involved in VEGF-mediated vascular morphogenesis using embryonic stem cell-derived cystic embryoid bodies," Laboratory investigation; a journal of technical methods and pathology, 2004, 84:1209-18, 10 pages.
Phng and Gerhardt, "Angiogenesis: a team effort coordinated by notch," Developmental Cell, Feb. 2009, 16(2):196-208.

\* cited by examiner

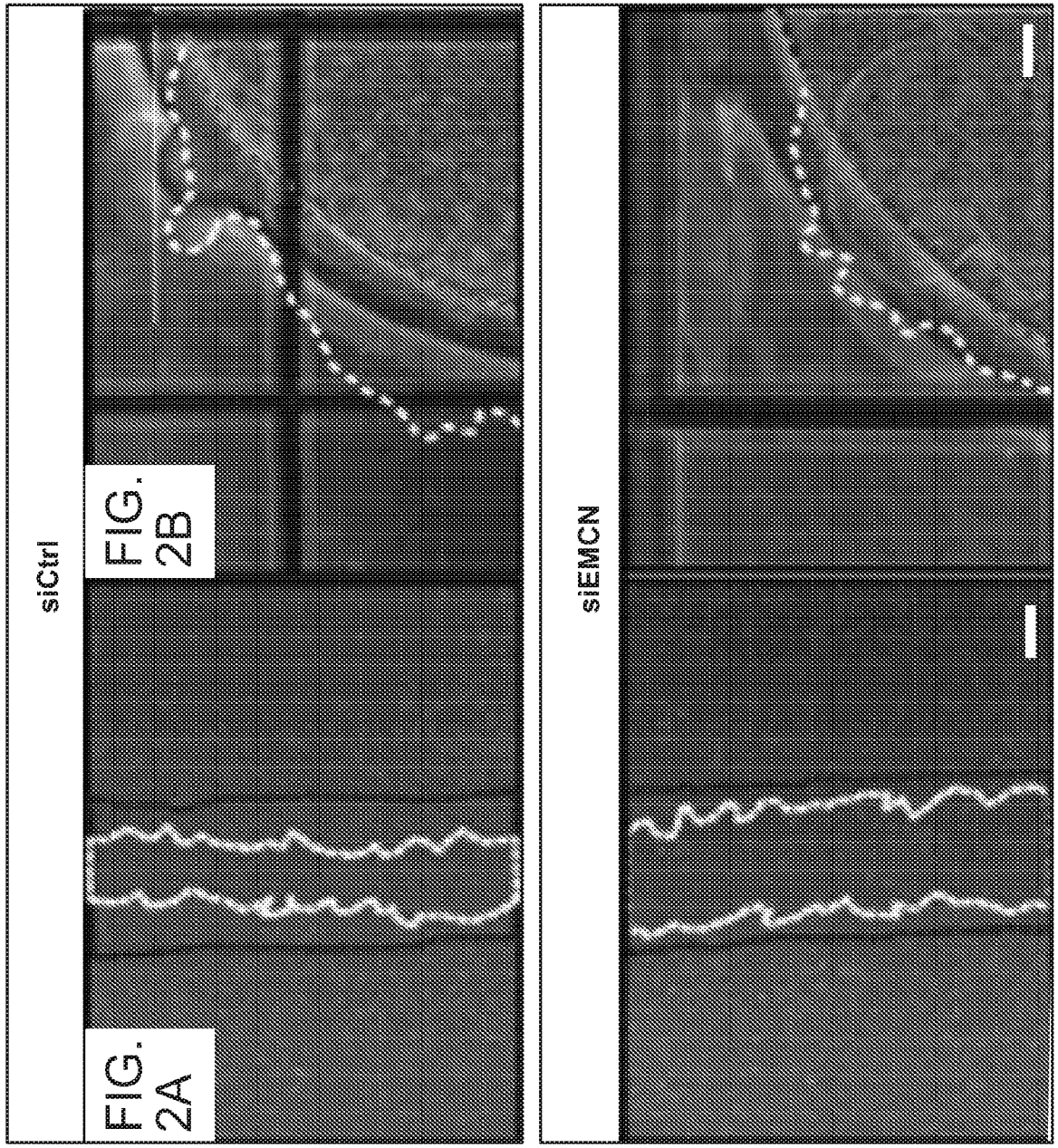

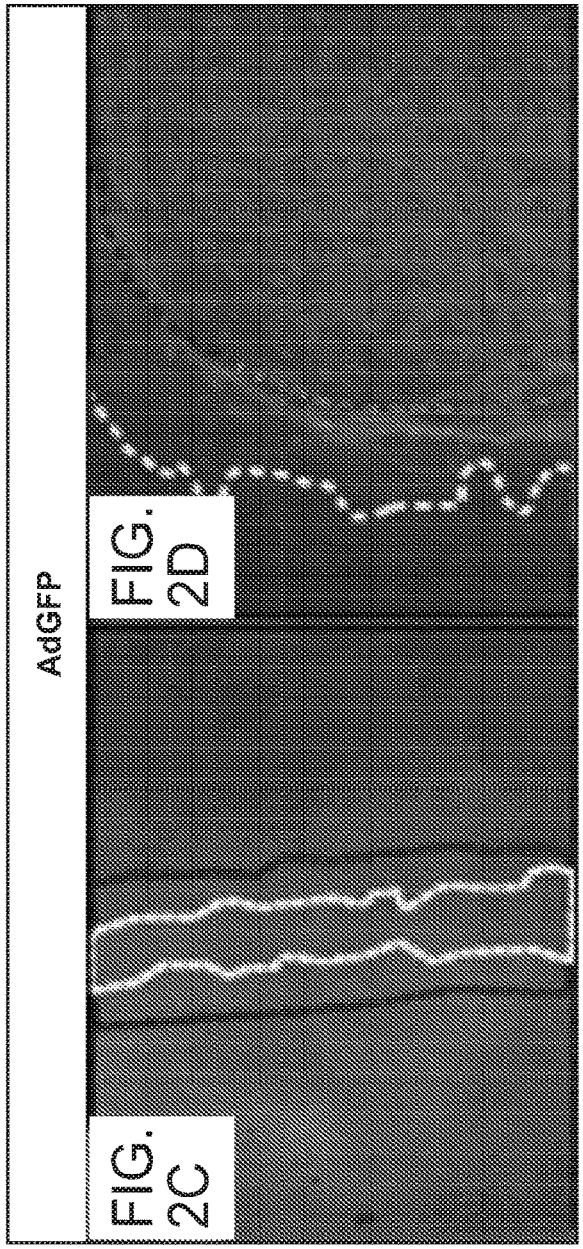
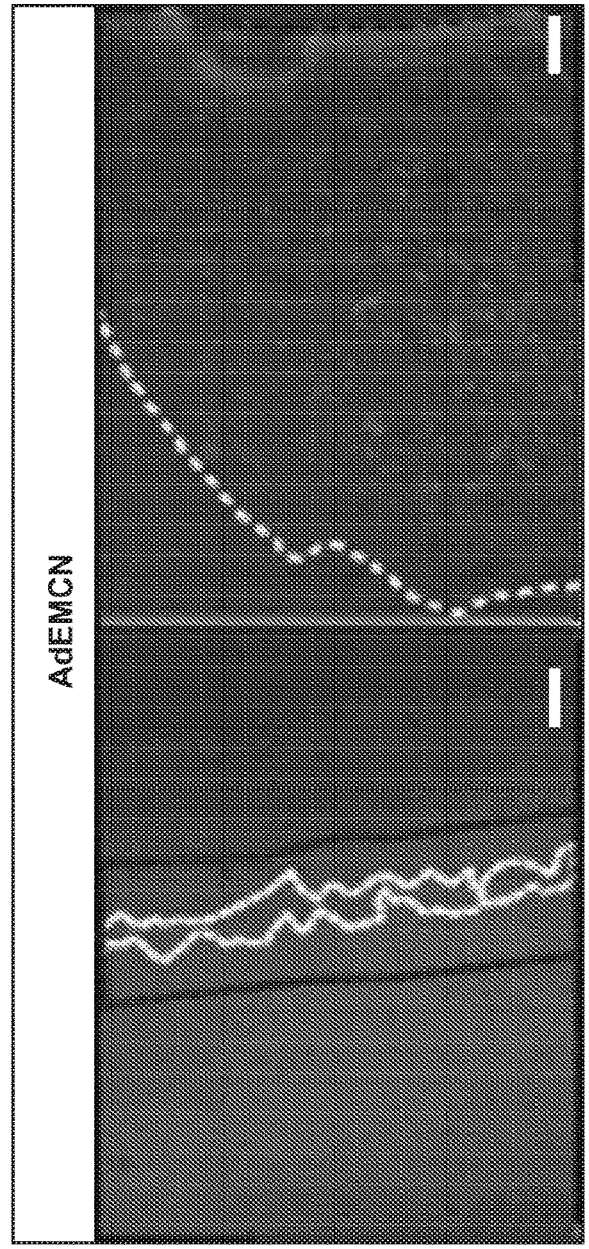

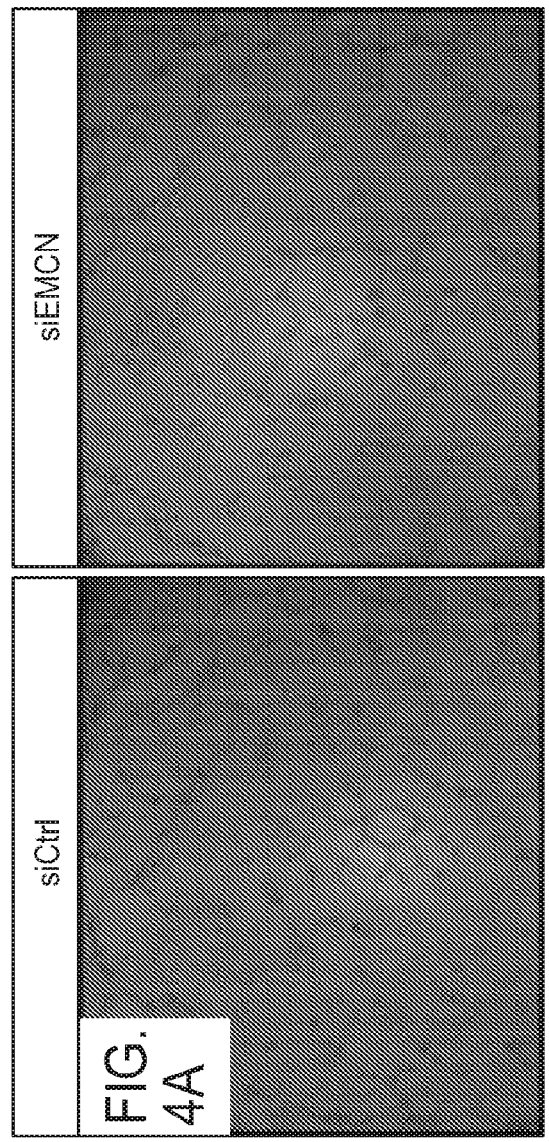
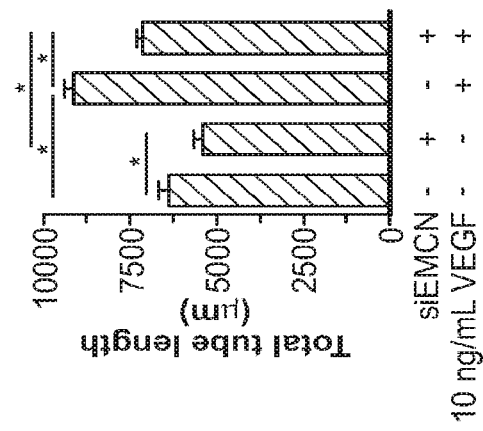
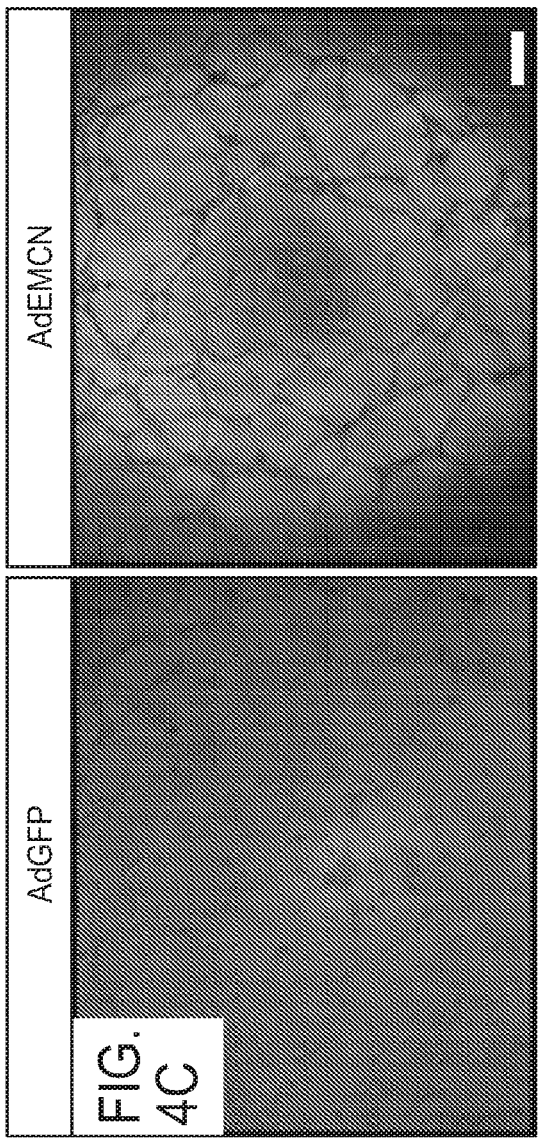
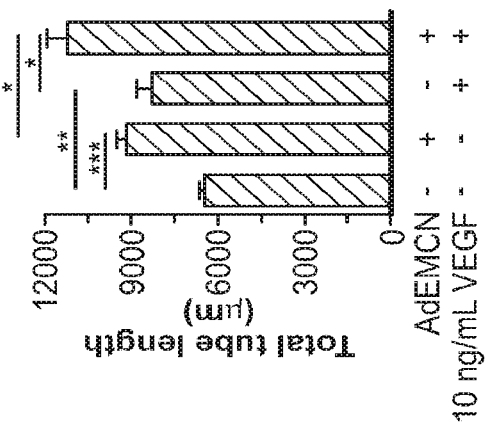

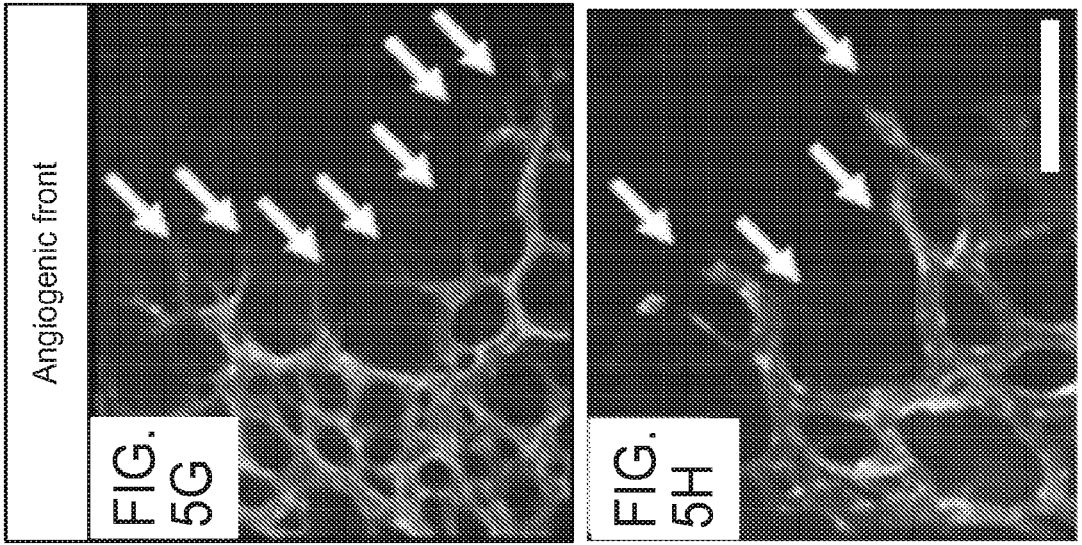
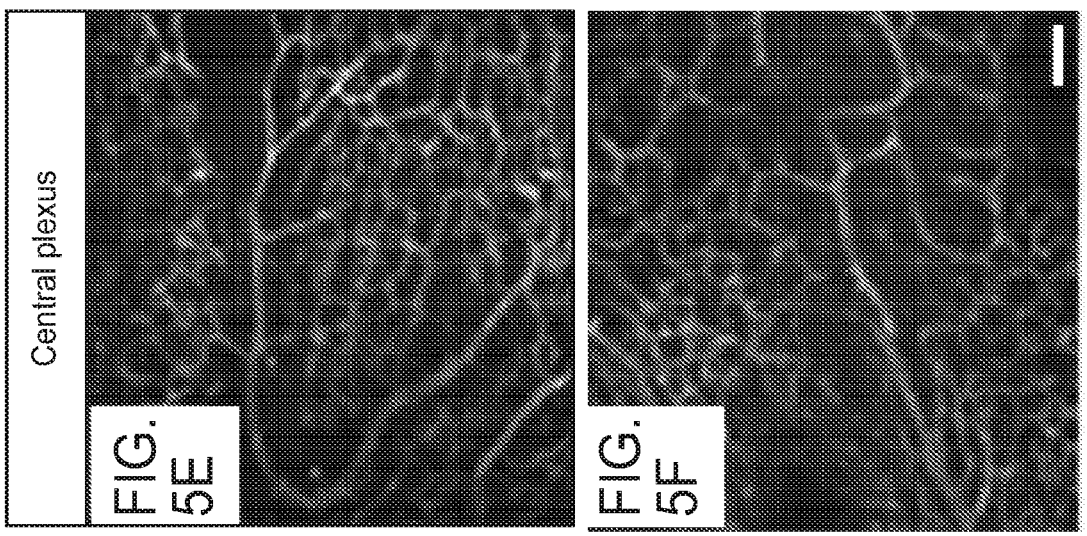

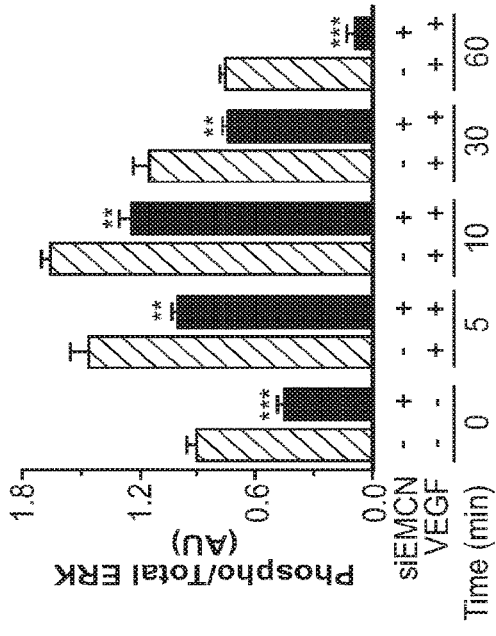
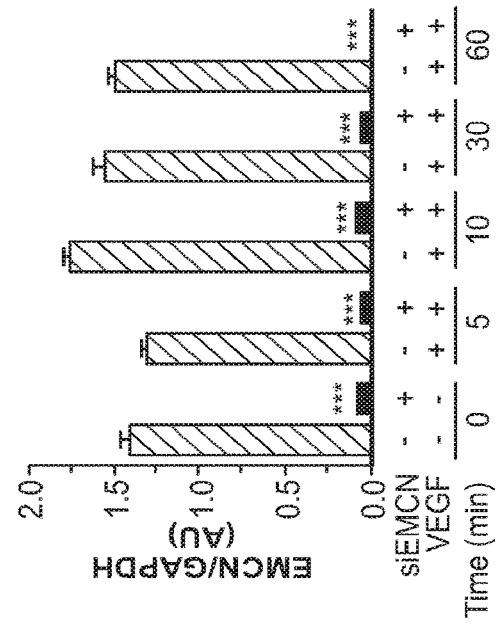
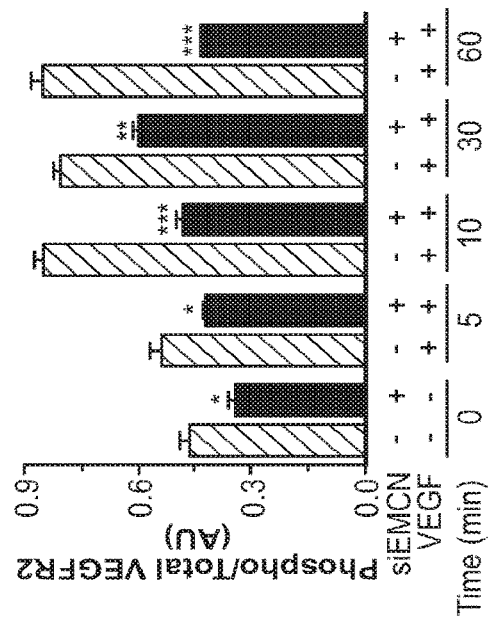
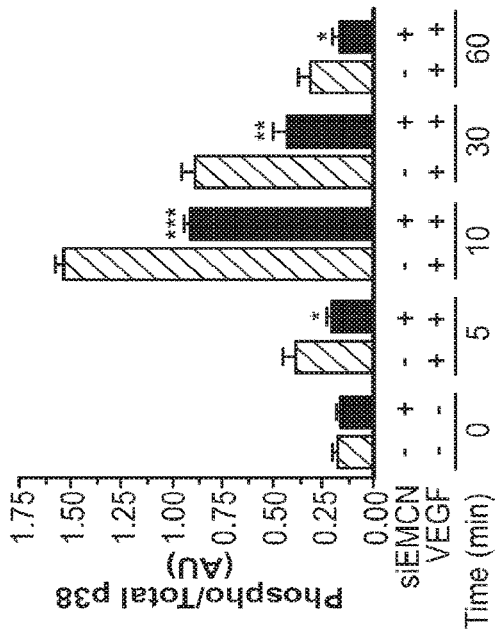

Avascular area

FIG. 7C
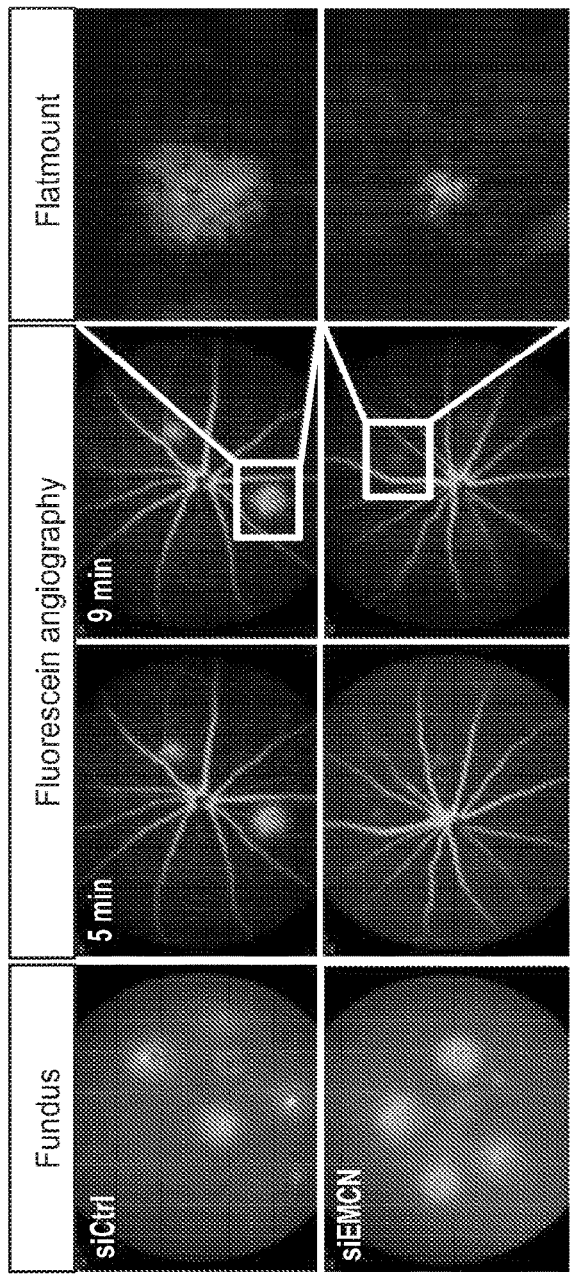
FIG. 7D Leakage area from laser lesions
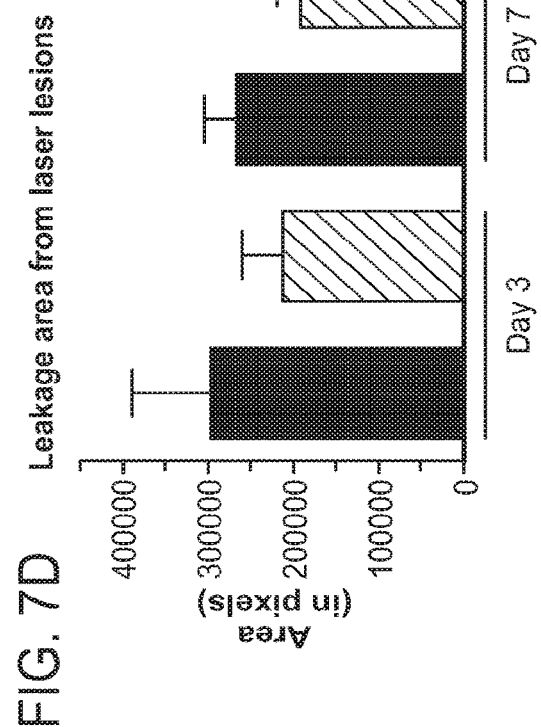
FIG. 7E CNV lesion size from choroidal mount
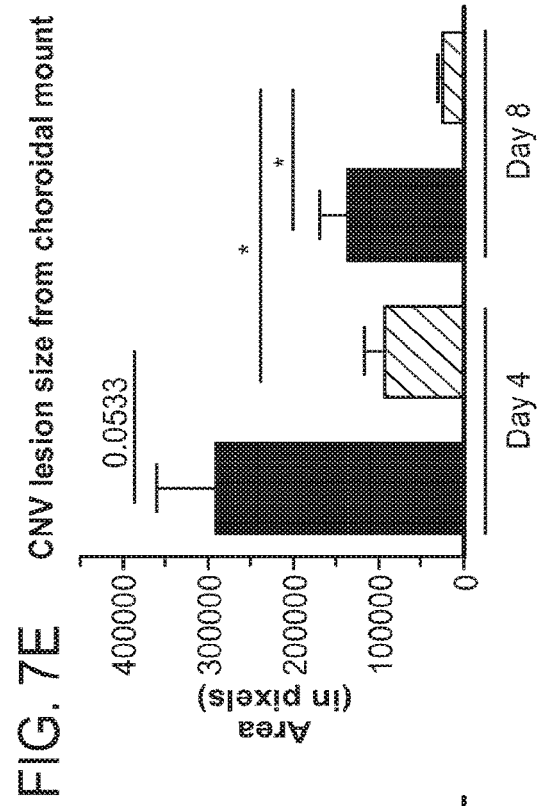

ENDOMUCIN INHIBITOR AS AN ANTI-ANGIOGENIC AGENT

CROSS-REFERENCES TO RELATED APPLICATIONS

This application is a divisional application of U.S. patent application Ser. No. 16/089,990, filed Sep. 28, 2018, now U.S. Pat. No. 10,883,108 issued Jan. 5, 2021, which is a national stage application filed under 35 U.S.C. § 371, of International Application No. PCT/US2017/025468, filed on Mar. 31, 2017, which claims the benefit of and priority under 35 U.S.C. § 119(e) to U.S. Provisional Application No. 62/316,481, filed on Mar. 31, 2016, the entire contents of which are incorporated herein by reference for all purposes.

FEDERAL FUNDING

This invention was made with government support under EY026539 awarded by the National Institutes of Health. The government has certain rights in the invention.

INCORPORATION BY REFERENCE OF SEQUENCE LISTING

The contents of the text file named 036770-552N01US_ST25.TXT, which was created on Sep. 28, 2018, and is 8,994 bytes in size, are hereby incorporated by reference in their entireties.

BACKGROUND OF THE INVENTION

Approximately 15 million Americans over the age of 65 suffer from AMD, and 10% of these patients will experience visual loss as a result of choroidal neovascularization. In addition, more than 16 million Americans are diabetic, and over 400,000 new patients suffer from retinal edema or neovascularization. The current number of 200 million diabetics worldwide is likely to double in the next 20 years. Of those patients over 8% suffer from microvascular complications.

BRIEF SUMMARY OF THE INVENTION

The invention provides a solution to a number of deficiencies or drawbacks associated with earlier methods to inhibit angiogenesis, e.g., aberrant angiogenesis, particularly in ocular tissue. For example, the invention provides compositions and methods with superior specificity for cells that mediate aberrant angiogenesis, e.g. neovascularization. The compositions and methods include an angiogenesis inhibitor that targets an endothelial cell specific-molecule, endomucin (EMCN). Endomucin-specific antiangiogenic treatments reduce and/or prevent progressive loss of vision as well as improve eyesight in patients.

Accordingly, the method for reducing neovascularization in an ocular tissue includes contacting the tissue with an inhibitor of EMCN expression or activity. For example, the inhibitor includes an EMCN-specific nucleic acid inhibitor such as a small interfering RNA (siRNA), e.g. UGGUUUA-CAUGUCGACUAA (SEQ ID NO: 1). Alternatively, anti-EMCN siRNA may comprise a sequence selected from SEQ ID Nos: 4-7. An siRNA molecule comprises a double stranded RNA that is about 10-30 base pairs, e.g., 20-25 base pairs in length. In embodiments, the inhibitor comprises at least one anti-EMCN shRNA. In embodiments, the inhibitor comprises at least one EMCN lentiviral particle gene silencer. In another embodiment, the inhibitor comprises an EMCN-specific antibody or fragment thereof or a small molecule inhibitor of EMCN. For example, the antibody or antigen-binding fragment thereof binds to an extracellular domain of EMCN. Such an antibody or antigen-binding fragment that binds to EMCN reduces, inhibits, and/or blocks the binding of VEGF to its receptor, VEGF-R.

The inhibitor preferentially or specifically reduces EMCN mRNA (or EMCN gene expression) in a cell or specifically reduces EMCN activity in the cell. In preferred embodiments, the inhibitor does not reduce VEGF gene expression or protein activity. The EMCN inhibitor reduces retinal neovascularization and/or choroidal neovascularization. The ocular tissue to be contacted with the inhibitor comprises endothelial cells, e.g., vascular endothelial cells in the eye.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a siRNA, (e.g., shRNA, miRNA, snoRNA), a peptide, a protein, compound or small molecule that inhibits cellular function (e.g., replication) e.g., by binding, partially or totally blocking stimulation, decrease, prevent, or delay activation, or inactivate, desensitize, or down-regulate signal transduction, gene expression or protein activity. An "endomucin (EMCN) inhibitor" refers to a substance that results in a detectably lower expression of endomucin gene or endomucin protein or lower activity level of endomucin protein as compared to those levels without such substance.

In embodiments, an EMCN inhibitor is an anti-endomucin siRNA. In embodiments, an EMCN inhibitor is an anti-endomucin shRNA. In embodiments, an EMCN inhibitor is an EMCN lentiviral particle gene silencer. In embodiments, an EMCN inhibitor is a small molecule compound. In embodiments, an EMCN inhibitor is an endomucin-specific antibody or fragment thereof. In embodiments, the endomucin-specific antibody or fragment thereof is an antagonist antibody or fragment thereof. In embodiments, an EMCN inhibitor is a composition (e.g., an anti-endomucin siRNA bound to a nanoparticle or a delivery vehicle) described herein. In embodiments, an EMCN inhibitor is a pharmaceutical composition described herein.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002).

Of the double stranded RNA of an siRNA, the strand that is at least partially complementary to at least a portion of a specific target nucleic acid (e.g. a target nucleic acid sequence), such as an mRNA molecule (e.g. a target mRNA molecule), is called the antisense (or guide strand; and the other strand is called sense (or passenger strand). The passenger strand is degraded and the guide strand is incorporated into the RNA-induced silencing complex (RISC).

The siRNA can be administered directly or siRNA expression vectors can be used to induce RNAi that have different design criteria. A vector can have inserted two inverted repeats separated by a short spacer sequence and ending with a string of T's which serve to terminate transcription.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

Aberrant or pathological angiogenesis, e.g., neovascularization, in the eye is associated with a number of ocular disorders. The inhibitor is useful to treat such disorders. For example, the inhibitor is administered to a subject suffering from or at risk of developing age-related macular degeneration (AMD), diabetic retinopathy (DR), retinopathy of prematurity (ROP), or ischemic retinal vein occlusion (IRVO). In some examples, the inhibitor is administered via injection, e.g., intravitreally, for a period of time, e.g., daily, monthly, every 4-6 weeks, or at prescribed intervals until clinical symptoms are improved or resolved. In other examples, the inhibitor is administered topically.

Subjects to be treated have been diagnosed with aberrant angiogenesis in the eye. For example, the subject is an infant such as a premature baby that has been exposed to high concentrations of oxygen, e.g., a child that is suffering from or is at risk of developing oxygen-induced retinopathy and/or has been diagnosed as such. In other examples, the subject is an adult who has been diagnosed with, is suffering from, or is at risk of developing any of the disorders listed above. For example in the context of AMD, e.g., wet AMD, the subject is at least 50 years of age, e.g., subject is at least 65 years of age.

In some embodiments, the method does not comprise administering an EMCN inhibitor to a heart, kidney, lung, or brain tissue. In some embodiments, the method does not include administration an EMCN inhibitor to a cancer or cancerous tissue. The method does however include administering the inhibitor to treat any of the aforementioned ocular diseases to a subject that comprises cancer in an anatomical location other than the eye.

Also within the invention is a composition comprising an endomucin inhibitor and a pharmaceutically-acceptable excipient suitable for administration to ocular tissue. For example, the inhibitor is formulated for injection into the eye, e.g., intravitreal injection. Suitable forms of the composition include a solid, a paste, an ointment, a gel, a liquid, an aerosol, a mist, a polymer, a film, an emulsion, or a suspension. In some cases, the composition is incorporated into or coated onto a contact lens. Preferably, the formulation is an aqueous formulation. The term "aqueous" typically denotes an aqueous composition wherein the carrier is to an extent of >50%, more preferably >75% and in particular >90% by weight water.

The compounds described for therapeutic use are purified. Purity is measured by any appropriate standard method, for example, by electrophoresis, column chromatography, thin layer chromatography, or high-performance liquid chromatography (HPLC) analysis. "Purified" also defines a degree of sterility that is safe for administration to a human subject, e.g., lacking infectious or toxic agents. For example, a purified compound is one that is at least 90%, 91%, 92%, 93%, 94%, 95%, 98%, 99%, or 100% (w/w) of the composition by weight.

A purified or isolated polynucleotide (ribonucleic acid (RNA) or deoxyribonucleic acid (DNA)) is free of the genes or sequences that flank it in its naturally-occurring state. For example, a purified DNA includes a cDNA. A purified or isolated polypeptide is free of the amino acids or sequences that flank it in its naturally-occurring state.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "natural amino acid" refers to a naturally occurring .alpha.-amino acid comprising a carbon atom bonded to a primary amino ($NH_2$) group, a carboxylic acid (COOH) group, a side chain, and a hydrogen atom. Exemplary natural amino acids include, but are not limited to, glycine, alanine, valine, leucine, isoleucine, methionine, phenylalanine, tryptophane, proline, serine, threonine, cysteine, tyrosine, asparaginate, glutaminate, aspartate, glutamate, lysine, arginine and histidine.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

Small molecule compounds are molecules less than 1000 daltons in molecular mass. Whether an organic compound or peptide, a small molecule compound is between 50-1000 daltons, e.g., less than 750 daltons, 500 daltons, 250 daltons or 100 daltons, in molecular mass. Small molecules include pharmaceutically active organic agents, biological agents, or peptides.

As used herein, "subject", as used herein, means a mammalian subject (e.g., dog, cat, horse, cow, sheep, goat, monkey, etc.), and particularly human subjects (including both male and female subjects, and including neonatal, infant, juvenile, adolescent, adult and geriatric subjects, and further including various races and ethnicities including, but not limited to, white, black, Asian, American Indian and Hispanic. In some embodiment, the human subject is an infant, e.g., less than 12 months of age, e.g., a neonatal infant or prematurely born infant, e.g, an infant that has been exposed to hyperoxic conditions. In some examples, the inhibitor is administered prior to, concurrent with, and/or shortly after (e.g., within 2, 4, 6, 12, 24 hours, 2, 3, 4, 5, or more days) after exposure to hyperoxic conditions. Follow on administration may continue weeks or months after hyperoxic treatment to reduce or remedy tissue damage. In other examples, the human subject is over the age of 50 years old, e.g., one that has been diagnosed with or is suffering from age-related macular degeneration. The inhibitor is administered to a subject at the acute phase, e.g., early in the disease progression or detection of symptoms by a clinician or subject. For example, an adult patient may seek medical assistance due to rapid loss of visual function. Administration of the inhibitor is carried out at presentation of such symptoms. Treatment continues for such subjects for days, weeks, months, or years as needed. For subjects diagnosed after an acute phase of a pathology (e.g., an acute insult such as hyperoxic conditions, an injury, or early stages of a chronic disease such as DR, AMD or IRVO), intervention/administration after an acute phase of inhibitors confer clinical benefit by reducing pathological angiogenesis as well as improving visual function. In embodiments, a subject is suffering from or at risk of developing diabetic retinopathy, age-related macular degeneration, retinopathy of prematurity, or ischemic retinal vein occlusion.

As used herein, "treatment", "treat", and "treating" refer to reversing, alleviating, inhibiting the progress, or delaying the progression of a condition, disorder or disease as described herein. For example, the condition is neovascularization. Neovascularization refers to aberrant or pathological angiogenesis, i.e., proliferation of blood vessels in a tissue not normally containing them and/or proliferation of blood vessels of a different kind than usual in a tissue. In embodiments, neovascularization is an ocular neovascularization (i.e., neovascularization within the eye).

In embodiments, ocular neovascularization is a retinal neovascularization. Retinal neovascularization occurs when there is retinal ischemia and leads to release of angiogenic factors like VEGF. Retinal neovascularization that occur within 1 disc diameter (DD) is considered as neovascularization of the disc and if further than 1 DD away, classified as neovascularization elsewhere (NVE). Common conditions that cause retinal neovascularization include: diabetic retinopathy, retinal vein occlusion, and ocular ischemic syndrome. Retinal neovascularization first develops in the intraretinal layers but will extend into the vitreous cavity and disrupt the inner limiting membrane (ILM) forming fibrovascular proliferations. SD-OCT when scanned over retinal neovascularization will reveal hyperreflective lesions that disrupt the ILM and protudes into the vitreous cavity connecting to the posterior hyaloid membrane if present.

In embodiments, ocular neovascularization is a choroidal neovascularization (CNV) (i.e., creation of new blood vessels in the choroid layer of the eye). CNV can occur rapidly in individuals with defects in Bruch's membrane, the innermost layer of the choroid. It is also associated with excessive amounts of vascular endothelial growth factor (VEGF), as well as in wet macular degeneration. CNV can also occur frequently with the rare genetic disease pseudoxanthoma elasticum and rarely with the more common optic disc drusen. CNV has also been associated with extreme myopia or malignant myopic degeneration, where in choroidal neovascularization occurs primarily in the presence of cracks within the retinal (specifically) macular tissue known as lacquer cracks.

As used herein, "prevention", "prevent", and "preventing" describes reducing or eliminating the onset of the symptoms or complications of the disease, condition or disorder.

As used herein "an effective amount" refers to an amount that causes relief of symptoms of a disorder or disease as noted through clinical testing and evaluation, subject observation, and/or the like. An "effective amount" can further designate a dose that causes a detectable change in biological or chemical activity. The detectable changes may be detected and/or further quantified by one skilled in the art for the relevant mechanism or process. Moreover, an "effective amount" can designate an amount that maintains a desired physiological state, i.e., reduces or prevents significant decline and/or promotes improvement in the condition of interest. In some embodiments, an "effective amount" can further refer to a therapeutically effective amount.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 1A is a bar graph showing EMCN mRNA expression (after siRNA knockdown). EMCN-siRNA resulted in 90% reduction at 24 hr and 48 hr in mRNA expression compared to non-targeting control siRNA (siCtrl). FIG. 1B is a photograph of an electrophoretic gel showing EMCN protein levels (after siRNA knockdown). EMCN-siRNA led to a 90% suppression of EMCN protein at 24 and 48 hr. FIG. 1C is a bar graph showing EMCN mRNA expression (after overexpression of EMCN). Exposure to AdEMCN resulted in a significant increase in EMCN mRNA (9-fold increase) at 24 and 48 hr compared to control after infection. FIG. 1D is a photograph of an electrophoretic gel showing EMCN protein levels (after overexpression of EMCN). Exposure to AdEMCN resulted in a significant increase in EMCN protein (10-fold increase) at 24 and 48 hr compared to control after infection. Results are representative from three independent experiments.$P<0.01$,*$P<0.001$ siEMCN vs siCtrl or AdEMCN vs AdGFP. Error bars represent SEM.

FIGS. 2A-2H. EMCN regulates VEGF-induced endothelial cell migration. HRECs were transfected with siCtrl, siEMCN, or infected with AdGFP or AdEMCN and cell migration was measured by a (FIGS. 2A, 2C) wound assay or an (FIGS. 2B, 2D) under-agarose assay. (FIG. 2A) Cells with reduced EMCN had reduced wound-closure (67% less than controls) at 10 hr post-wounding while (FIG. 2C) AdEMCN infected cells exhibited a 1.4-fold increase in migration after 10 hrs when compared with AdGFP control cells. (FIG. 2B) HREC in which EMCN was knocked down with siEMCN migrated up to 0.5 mm from the starting point while control cells (treated with siCtrl) migrated up to 2.3 mm (FIG. 2D) The migration of AdEMCN infected cells In response to VEGF at 36 hr was increased 2.6-fold compared to that of AdGFP-infected control cells. Results are from four independent experiments in triplicate. *$P<0.05$, ***$P<0.001$ siEMCN vs siCtrl or AdEMCN vs AdGFP. Error bars represent SEM. Scale bar 500 μm. FIG. 2E is a bar graphs showing percent scratch closure. FIG. 2F is a bar graph showing mean distance moved. FIG. 2G is a bar graph showing percent scratch closure. FIG. 2 H is a bar graph showing mean distance moved.

(FIG. 3A) In the presence of VEGF (10 ng/mL), the cells were viable and EMCN-deficient cells displayed a significant decrease in cell proliferation (a 50% decrease) compared to control cells. (FIG. 3B) Reduced EMCN mRNA expression was confirmed at each time-point. (FIG. 3C) Cells infected with AdEMCN resulted in an increase in cell proliferation compared to AdGFP cells. (FIGS. 3D-3E) Cytofluorimetric analysis of annexin V in HRECs showed no change in total apoptotic events in EMCN-reduced cells compared with the control cells. Results are from three independent experiments in triplicate. *$P<0.05$, $P<0.01$, *$P<0.001$ siEMCN vs siCtrl or AdEMCN vs AdGFP. Error bars represent SEM.

FIGS. 4A-4D. EMCN expression modulates VEGF-induced tube morphogenesis by HRECs. (FIGS. 4A-4B) Results demonstrated that tube formation by EC with reduced EMCN was inhibited by approximately 22% and 18% in the absence or presence of VEGF after 6 hr, respectively. FIG. 4A is photographs of tube morphogenesis in experimental groups treated by control siRNA (left panel) or EMCN-siRNA (right panel). FIG. 4B is a bar graph showing tube length. (FIGS. 4C-4D) Conversely, the morphogenic response of AdEMCN infected cells was more increased 1.4- and 1.3-fold increase over that observed in AdGFP control cells in the absence or presence of VEGF at 6 hr, respectively. FIG. 4C is photographs of tube morphogenesis in experimental groups treated by AdGFP (left panel) or AdEMCN (right panel).

FIG. 4D is a bar graph showing tube length. Quantitative results are from three independent experiments. *$P<0.05$, ***$P<0.001$ siEMCN vs siCtrl or AdEMCN vs AdGFP; *$P<0.05$, **$P<0.01$ VEGF vs no VEGF. Error bars represent SEM. Scale bar 100 μm.

FIGS. 5A-5L. Loss of EMCN results in defective retinal vascular development. P4 mice injected with siEMCN and scarified at P6 showed (FIGS. 5A-5B and 5I) a reduced vascular plexus from the optic nerve head to the periphery indicative of impaired angiogenesis compared to siCtrl-injected mice. To further analyze the apparent impairment of angiogenesis caused by the knockdown of EMCN, we examined (FIG. 5J) vessel density, (FIG. 5K) branch point number, and (FIG. 5L) tip cell number in P6 retinas. FIG. 5A-5B are photographs showing whole vascular plexus in the retina. FIGS. 5C-5D are photographs showing quadrant vascular plexus in the retina. FIGS. 5E-5F are photographs showing central plexus in the retina. FIGS. 5G-5H are photographs showing angiogenic front in the retina. FIG. 5I is a bar graph showing vascularized area. FIG. 5J is a bar graph showing retinal vascular density. FIG. 5K is a bar graph showing number of branchpoints per field. FIG. 5L is a bar graph showing filopodia per 100 μm. All of these endpoints were significantly decreased in siEMCN-injected mice compared with littermate siRNA control injected mice. *$P<0.05$,  $P<0.01$, *$P<0.001$ siEMCN vs siCtrl. Error bars represent SEM. Scale bar 100 μm.

FIGS. 6A-6E. EMCN controls angiogenesis by altering VEGFR2 activation. HRECs with or without siEMCN-mediated knockdown were stimulated with exogenous VEGF (10 ng/mL) and assessed for levels of VEGFR2 phosphorylation by (FIG. 6A) immunoblot. (FIG. 6B) VEGF treatment of cells with reduced EMCN displayed a 45% reduction in VEGFR2 phosphorylation compared to siCtrl cells. The level of phospho-VEGFR2 was also depressed in siEMCN treated cells compared to siCtrl cells in the absence of VEGF challenge. Examination of the effect of EMCN knockdown on the activation of (FIG. 6C) ERK1/2 and (FIG. 6D) p38-MAPK revealed a decrease in phospho-ERK1/2 and phospho-p38-MAPK expression in EMCN-deficient cells in response to VEGF treatment. FIG. 6A is a photograph showing the results of an immunoblot assay. FIG. 6B is a bar graph showing VEGFR2 phosphorylation (phospho/total VEGFR2). FIG. 6C is a bar graph showing the effect of EMCN knockdown on phospho-ERK (phosphor/total ERK). FIG. 6D is a bar graph showing the effect of EMCN knockdown on phospho-p38 (phosphor/total p38). FIG. 6E is a bar graph showing EMCN/GADPH. *$P<0.05$, $P<0.01$, *$P<0.001$. Error bars represent SEM.

FIGS. 7A-7E. Loss of EMCN is protective against oxygen-induced retinopathy (OIR) and choroidal neovascularization (CNV). FIGS. 7A-7B show that inhibition of EMCN results in inhibition of pathological neovascularization when mice were exposed to hyperoxia. Quantification of neovascular area demonstrated a robust inhibition of pathological neovascularization at P17 (FIG. 7A). Quantification of the avascular areas shows decreased vaso-obliteration at P17 indicating improved physiological revascularization of avascular areas as indicated by the increased slope value (FIG. 7B). To further analyze the effect of EMCN under pathological conditions, mice underwent laser treatment and siEMCN injection. Extent of leakage (FIGS. 7C and 7D) and lesion size (FIG. 7E) were significantly decreased in siEMCN-injected mice compared with littermate siRNA control injected mice. *$P<0.05$, ***$P<0.001$ siEMCN vs siCtrl. Error bars represent SEM.

DETAILED DESCRIPTION OF THE INVENTION

Figure 1A:
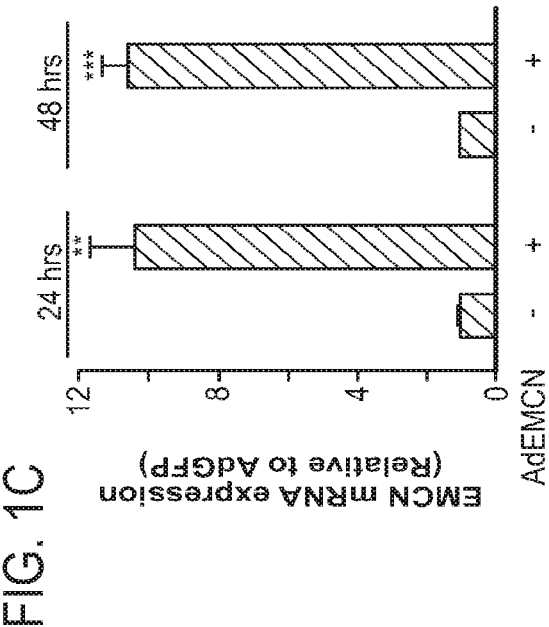
FIGS. 1A-1D. Knockdown and over-expression of EMCN on human retinal EC (HREC).

Angiogenesis is the development of new capillary networks from the normal vasculature and is a fundamental process during embryogenesis. In adulthood, angiogenesis contributes to corpus luteum formation, placental implantation and wound healing and is also involved in some pathological conditions such as several intraocular syndromes, growth of solid tumors, and metastasis. Many factors are involved in the regulation of neovascularization among which FGF-2 (fibroblast growth factor-2) and VEGF (vascular endothelial growth factor) are considered as key inducers.

In the process of angiogenesis, new vessels grow from existing vessels via branching morphogenesis. Glycoproteins are believed to influence a variety of events such as angiogenesis, making them useful therapeutic targets for a broad range of pathologic conditions. Endothelial cells (ECs) express high levels of 0-glycoproteins that that are involved in vascular development and stability. However prior to the invention, there was a significant gap in knowledge regarding which specific glycoproteins are involved in regulating vascular development and the role(s) that they play. According to the invention, EMCN, a highly 0-glycosylated glycoprotein, is targeted to inhibit or prevent pathological angiogenesis. A reduction or loss of EMCN results in defective retinal vascular development in vivo.

Anti-angiogenic drugs exert their beneficial effects in a number of ways: by disabling the agents that activate and promote cell growth, or by directly blocking the growing blood vessel cells. However prior to this invention, the mechanisms and genes involved in the suppression or attenuation of angiogenic processes were not well understood. As such, there is significant need to develop new anti-angiogenic therapies. The invention described herein includes compositions and methods that target EMCN, which is specifically expressed in endothelial cells, thereby providing an anti-angiogenic therapy with high specificity for regions of active aberrant neovascularization. For example, the compositions and methods described herein inhibit/reduce aberrant angiogenesis (i.e., neovascularization), because EMCN inhibition preferentially targets active and proliferating endothelial cells compared to normal, inactive or quiescent endothelial cells.

EMCN is a sialic-rich glycoprotein and a component of the endothelial glycocalyx. EMCN is expressed by the venous and capillary but not by arterial endothelium. EMCN gene expression in the endothelium was shown to be downregulated in a screen of cystic embryoid bodies generated from vascular endothelial growth factor (VEGF) null embryonic stem cells. Studies of EMCN regulation also reveal that its expression is increased during proliferation or following stimulation with tumor-conditioned media and by factors such as basic fibroblast growth factor and that GATA2-regulated EMCN gene expression may be involved in vessel formation. The data described herein reveals a novel function for EMCN in the regulation of proangiogenic signaling in EC migration, proliferation, and vessel morphogenesis in vitro and that EMCN interferes with normal developmental angiogenesis in vivo.

ECs heavily express O-glycoproteins and in particular express high levels of EMCN and EMCN is a major contributor in pathological vessel formation. EMCN plays a role in regulating retinal angiogenesis, and thus methods to modulate EMCN expression and/or activity are useful to treat retinopathy.

Endomucin

EMCN is a mucin-like sialoglycoprotein. The deduced 261-amino acid protein has a calculated molecular mass of 27.5 kD. EMCN contains an N-terminal signal peptide, followed by a uteroglobin homology domain, a phosphatidylinositol 3-kinase RAS-binding domain, and a C-terminal transmembrane domain. The N terminus is extracellular, and the C terminus is intracellular. EMCN has several sites for N-glycosylation, N-myristoylation, and phosphorylation. Mouse and human EMCN share 49% amino acid homology.

An "EMCN gene" as referred to herein includes any of the recombinant or naturally-occurring forms of the gene encoding endomucin (EMCN), fragments, homologs or variants thereof that maintain EMCN protein activity (e.g. within at least 50%, 80%, 90%, 95%, 96%, 97%, 98%, 99% or 100% activity compared to EMCN). In embodiments, an EMCN gene encodes a variant having at least 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EMCN polypeptide (NCBI reference number: NP_001153166 or NP_057326). In embodiments, the EMCN gene is 70%, 75%, 80%, 85%, 90%, 95%, 96%, 97%, 98%, 99% or 100% identical to the nucleic acid sequence identified by the NCBI reference number NM_001159694 or NM_016242 or a variant having substantial identity thereto.

An "EMCN" as referred to herein includes any of the recombinant or naturally-occurring forms of endomucin (EMCN), fragments, homologs or variants thereof that maintain EMCN protein activity (e.g. within at least 50%, 80%, 90%, 95%, 96%, 97%, 98%, 99% or 100% activity compared to EMCN). In embodiments, EMCN variants have at least 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EMCN protein. In embodiments, variants have at least 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to amino acid sequence identified by NCBI reference number: NP_001153166 or NP_057326.

The term "fragment," as used herein, means a portion of a polypeptide or polynucleotide that is less than the entire polypeptide or polynucleotide. As used herein, a "functional fragment" of a protein, e.g., EMCN, is a fragment of the polypeptide that is shorter than the full-length, immature, or mature polypeptide and has at least 25% (e.g., at least 30%, 40%, 50%, 60%, 70%, 80%, 90%, 95%, 98%, 99%, or even 100% or more) of the activity of full-length mature reference protein. Fragments of interest can be made by recombinant, synthetic, or proteolytic digestive methods. A nucleic acid fragment of almost any length is employed. For example, illustrative polynucleotide segments with total lengths of about 4,000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 225, about 100, about 50, about 25, or about 10-12 amino acids in length (including all intermediate lengths) are included in many implementations of this invention.

Fragments are less than 261 amino acids (full length). For example, a fragment includes the signal peptide of EMCN-1, e.g., amino acids 1-18 of full length EMCN-1 (e.g., SEQ ID NO: 2). Alternatively, a fragment comprises amino acids 19-261 of full length EMCN-1 (e.g., SEQ ID NO: 2). Exemplary amino acid fragments include those that comprise the extracellular domain of EMCN-1, i.e., amino acids 19-190 (e.g., amino acids 19-190 of SEQ ID NO: 2). For example, a fragment of EMCN-1 comprises amino acids 70-181; amino acids 70-89; or amino acids 173-181 of full length EMCN-1 (e.g., SEQ ID NO: 2). Suitable fragments also include those that comprise the transmembrane of EMCN-1 (e.g., SEQ ID NO: 2), i.e., amino acids 191-211. Other suitable fragments include those that comprise the cytoplasmic domain of EMCN-1 (e.g., SEQ ID NO: 2), i.e., amino acids 212-261. For example, a fragment of EMCN-1 comprises amino acid 237 of full length EMCN-1 (e.g., SEQ ID NO: 2). In some cases, exemplary fragments include a glycosylated amino acid at position 19, 28, 98, 104, 164, or 178 of full length EMCN-1 (e.g., SEQ ID NO: 2). In other cases, exemplary fragments include a phosphorylated amino acid at position 70, 76, 80, 173, 180, 181, or 237 of full length EMCN-1 (e.g., SEQ ID NO: 2).

An exemplary human Endomucin amino acid sequence (*Homo sapiens* endomucin (EMCN), endomucin isoform 1 precursor, NCBI Reference Number: NP_057326.2, hereby incorporated by reference) is listed below.

```
                                                    (SEQ ID NO: 2)
MELLQVTILFLLPSICSSNSTGVLEAANNSLVVTTTKPSITTPN

TESLQKNVVTPTTGTTPKGTITNELLKMSLMSTATFLTSKDEGLKATTT

DVRKNDSIISNVTVTSVTLPNAVSTLQSSKPKTETQSSIKTTEIPGSVL

QPDASPSKTGTLTSIPVTIPENTSQSQVIGTEGGKNASTSATSRSYSSI

ILPVVIALIVITLSVFVLVGLYRMCWKADPGTPENGNDQPQSDKESVKL

LTVKTISHESGEHSAQGKTKN
```

Underlined characters represents signal sequence (residues 1-18). Residues 19-190 correspond to the extracellular domain of EMCN. Residues 191-211 correspond to the transmembrane domain. Residues 212-261 correspond to the cytoplasmic domain.

An exemplary human Endomucin nucleic acid sequence (*Homo sapiens* endomucin (EMCN), transcript variant 1, mRNA; NCBI Reference Sequence: NM_016242.3, hereby incorporated by reference) is listed below.

```
                                                      (SEQ ID NO: 3)
  1   gggagtgtgt gtatttcctc ccgttcttta tcagagcccc caaaataagt aggaatgggc 61   agtggctatt cacattcact acacctttc catttgctaa taaggccctg ccaggctggg 121   agggaattgt ccctgcctgc ttctggagaa agaagatatt gacaccatct acgggcacca 181   tggaactgct tcaagtgacc attcttttc ttctgcccag tatttgcagc agtaacagca 241   caggtgtttt agaggcagct aataattcac ttgttgttac tacaacaaaa ccatctataa 301   caacaccaaa cacagaatca ttacagaaaa atgttgtcac accaacaact ggaacaactc 361   ctaaaggaac aatcaccaat gaattactta aaatgtctct gatgtcaaca gctactttt 421   taacaagtaa agatgaagga ttgaaagcca caaccactga tgtcaggaag aatgactcca 481   tcatttcaaa cgtaacagta acaagtgtta cacttccaaa tgctgtttca acattacaaa 541   gttccaaacc caagactgaa actcagagtt caattaaaac aacagaaata ccaggtagtg 601   ttctacaacc agatgcatca ccttctaaaa ctggtacatt aacctcaata ccagttacaa 661   ttccagaaaa cacctcacag tctcaagtaa taggcactga gggtggaaaa aatgcaagca
```

-continued

```
 721   cttcagcaac cagccggtct tattccagta ttattttgcc ggtggttatt gctttgattg
 781   taataacact ttcagtattt gttctggtgg gtttgtaccg aatgtgctgg aaggcagatc
 841   cgggcacacc agaaaatgga aatgatcaac ctcagtctga taaagagagc gtgaagcttc
 901   ttaccgttaa gacaatttct catgagtctg gtgagcactc tgcacaagga aaaccaaga
 961   actgacagct tgaggaattc tctccacacc taggcaataa ttacgcttaa tcttcagctt
1021   ctatgcacca agcgtggaaa aggagaaagt cctgcagaat caatcccgac ttccatacct
1081   gctgctggac tgtaccagac gtctgtccca gtaaagtgat gtccagctga catgcaataa
1141   tttgatgaa tcaaaagaa ccccggggct ctcctgttct ctcacattta aaaattccat
1201   tactccattt acaggagcgt tcctaggaaa aggaattta ggaggagaat tgtgagcag
1261   tgaatctgac agcccaggag gtgggctcgc tgataggcat gactttcctt aatgtttaaa
1321   gttttccggg ccaagaattt ttatccatga agactttcct acttttctca gtgttcttat
1381   attacctact gttagtattt attgtttacc actatgttaa tgcagggaaa agttgcacgt
1441   gtattattaa atattaggta gaaatcatac catgctactt tgtacatata agtattttat
1501   tcctgctttc gtgttacttt taataaataa ctactgtact caatactcta aaaatactat
1561   aacatgactg tgaaaatggc aatgttattg tcttcctata attatgaata tttttggatg
1621   gattattaga atacatgaac tcactaatga aaggcatttg taataagtca gaagggaca
1681   tacgattcac atatcagact gttaggggga gagtaattta tcagttcttt ggtctttcta
1741   tttgtcattc atactatgtg atgaagatgt aagtgcaagg gcatttataa cactatactg
1801   cattcattaa gataataggga tcatgatttt tcattaactc atttgattga tattatctcc
1861   atgcatttt tatttctttt agaaatgtaa ttatttgctc tagcaatcat tgctaacctc
1921   tagtttgtag aaaatcaaca cttataaat acataattat gatattattt tcattgtat
1981   cactgttcta aaaataccat atgattatag ctgccactcc atcaggagca aattcttctg
2041   ttaaaagcta actgatcaac cttgaccact tttttgacat gtgagatcaa agtgtcaagt
2101   tggctgaggt tttttggaaa gctttagaac taataagctg ctggtggcag ctttgtaacg
2161   tatgattatc taagctgatt ttgatgctaa attatcttag tgatctaagg ggcagtttag
2221   tgaagatgga atcttgtatt taaaatagcc ttttaaaatt tgttttgtgg tgatgtattt
2281   tgacaacttc catctttagg agttatataa tcaccttgat tttagtttcc tgatgtttgg
2341   actatttata atcaaggaca ccaagcaagc ataagcatat ctatatttct gactggtgtc
2401   tctttgagaa ggatgggaag tagaaaaaaa aaaagaaag aaggaaagg aagagaggag
2461   agaagaaggc agggatctcc actatgtatg ttttcacttt agaactgttg agcccatgct
2521   taattttaat ctagaagtct ttaaatggtg agacagtgac tggagcatgc caatcagaga
2581   gcatttgtct tcagaaaaaa aaaaaatctg agtttgagac tagcctggcc aacatgttga
2641   aaccccatat ctactaaaaa tacaaaaatt agcctggtgt ggtggcgcac gcctgtagtc
2701   ccagctactc tggagcctga ggaacgtgaa tcgcttgaac ccagaagaca gaggttgcag
2761   tgagctgaga tggcactatt gcactccagc ctgggtgaca cagcaagact ctgtctcaaa
2821   aaaaaaaaa aaaaaagga aaaaaagaa agaagaaag tcccagcaca cctagataat
2881   ttaccgagct cttcagcaaa aaccatgtta catacagcat attccaaaga aatgaactct
2941   tctgcaattt aaattataag taatatgtta ttttggatcc tagagaaacc attttctcta
3001   catttcatga gcatggttag aaaagagttt acaagaatta ggaagaggga acaattttaa
3061   tggtcagaaa agaataaaat ttattctagt tcaagaagtg cacacaaaga atatgcatta
3121   atctaacaac tatgagatta aatctttcaa aaaggtcaaa ggaggattga gaagtttaca
```

```
3181   gagatgtcca cggcatttta tatcaatctc aaaggtaagg tctgcatttt tataaaccaa 3241   cttaaacttc tgttgagata ggatattttg ttttcaagcc aaaattacca ttaatcaaat 3301   atgttttaat tatctgattt agatgatcta cttttatgc ctggcttact gtaagttttt 3361   tattctgata cacagttcaa acatcattgc aacaaagaag tgcctgtatt tagatcaaag 3421   gcaagacttt ctatgtgttt gttttgcata ataatatgaa tataatttaa gtctatcaat 3481   agtcaaaaca taaacaaaag ctaattaact ggcactgttg tcacctgaga ctaagtggat 3541   gttgttggct gacatacagg ctcagccagc agagaaagaa ttctgaattc cccttgctga 3601   actgaactat tctgttacat atggttgaca aatctgtgtg ttatttcttt tctacctacc 3661   atatttaaat ttatgagtat caaccgagga catagtcaaa ccttcgatga tgaacattcc 3721   tgattttttg cctgattatt ctctgttgag ctctacttgt ggtcattcaa gattttatga 3781   tgttgaaagg aaaagtgaat atgaccttta aaaattgtat tttgggtgat gatagtctca 3841   ccactataaa actgtcaatt attgcctaat gttaaagata tccatcattg tgattaatta 3901   aacctataat gagtattctt aatggagaat tcttaatgga tggattatcc cctgatcttt 3961   tctttaaaat ttctctgcac acacaggact tctcattttc caataaatgg gtgtactctg 4021   ccccaatttc tagggaaaaa aaaaaaa
```

Nucleic acids 180-233 encode a signal sequence; nucleic acids 234-962 encode mature peptide/protein; nucleic acids 750-812 encode transmembrane domain.

Additional description of EMCN is provided in U.S. Patent Pub. No. 2015/0018267; hereby incorporated by reference.

Compositions and Pharmaceutical Compositions

Provided herein is a composition including an endomucin (EMCN) inhibitor and a pharmaceutically-acceptable excipient suitable for administration to ocular tissues.

In embodiments, EMCN inhibitor described herein is an EMCN-specific nucleic acid inhibitor. In embodiments, EMCN inhibitor described herein includes at least one EMCN-specific siRNA inhibitor. In embodiments, EMCN inhibitor described herein includes at least two or more (e.g., 2, 3, 4, 5, 6, 7, 8, 9, 10, 11, 12, 13, 14, 15, 16, 17, 18, 19, 20 or more) EMCN-specific siRNA inhibitors. In embodiments, EMCN inhibitor described herein includes at least one (e.g., 1, 2, 3, 4 or 5) of sequences of SEQ ID Nos: 1 and 4-7.

As used herein, the term "EMCN-specific siRNA" or "anti-EMCN siRNA" includes all forms of anti-EMCN siRNA, including variants, modifications and derivatives thereof. In embodiments, the siRNA molecule is an oligonucleotide with a length of about 19 to about 35 base pairs (e.g., about 19, 20, 21, 22, 23, 24, 25, 26 27, 28, 29, 30, 31, 32 33, 34, 35 base pairs). In another embodiment, the molecule is an oligonucleotide with a length of about 19 to about 27 base pairs. In embodiments, the molecule is an oligonucleotide with a length of about 20 to about 25 base pairs. In embodiments, the molecule may have blunt ends at both ends, or sticky ends at both ends, or a blunt end at one end and a sticky end at the other. In embodiments, an anti-EMCN siRNA targets EMCN isoform 1 or variants and homologues. In embodiments, an anti-EMCN siRNA targets EMCN isoform 2 or variants and homologues. In embodiments, an anti-EMCN siRNA targets both EMCN isoform 1 and EMCN isoform 2 or their variants and homologues. Exemplary anti-EMCN siRNA sequences can be found below (e.g., SEQ ID Nos 4-7). One skilled in the art will appreciate that anti-EMCN siRNAs of the invention also include sequences having about 95%, about 96%, about 97%, about 98%, about 99% identity to any one of SEQ ID Nos: 1 and 4-7.

As described above, antisense nucleic acids are capable of hybridizing to (e.g. selectively hybridizing to) a target nucleic acid (e.g. target mRNA). In some embodiments, the antisense nucleic acid hybridizes to the target nucleic acid sequence (e.g. mRNA) under stringent hybridization conditions. In some embodiments, the antisense nucleic acid hybridizes to the target nucleic acid (e.g. mRNA) under moderately stringent hybridization conditions.

An siRNA sequence (including antisense or sense sequence) may comprise naturally occurring nucleotides or modified nucleotides. Examples of such modifications include chemical substitutions at the ribose and/or phosphate and/or base positions. Modified nucleotides are described in U.S. Pat. No. 5,660,985, which describes oligonucleotides containing nucleotide derivatives chemically modified at the 2' position of ribose, 5 position of pyrimidines, and 8 position of purines. U.S. Pat. No. 5,756,703 describes oligonucleotides containing various 2'-modified pyrimidines. U.S. Pat. No. 5,580,737 describes highly specific nucleic acid ligands containing one or more nucleotides modified with 2'-amino (2'-NH$_2$), 2'-fluoro (2'-F), and/or 2'-O-methyl (2'-OMe) substituents.

Modifications of the siRNA sequences contemplated in this invention include, but are not limited to, those which provide other chemical groups that incorporate additional charge, polarizability, hydrophobicity, hydrogen bonding, electrostatic interaction, and fluxionality to the siRNA bases or to the siRNA sequences as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications may also include 2'-O-methyl modifications, 2'-O-methyl modified ribose sugars with terminal phosphorothioates and a cholesterol group at the 3' end, 2'-O-methoxyethyl (2'-MOE) modifications, 2'-fluoro modifications, and 2',4' methylene modifications (referred to as "locked nucleic acids" or LNAs). Modifications can also include 3' and 5' modifications such as capping.

In embodiments, EMCN inhibitors provided herein are anti-EMCN shRNAs. The term "hairpin dsRNA", a "dsRNA hairpin," "short-hairpin RNA" or "shRNA", used herein interchangeably, refers to an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 500 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 250-500 bp, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence. Exemplary anti-EMCN shRNA includes, but is not limited to, anti-EMCN shRNA obtained from Santa Cruz Biotechnology, Inc. (Cat. No. sc-43156-SH) and Dharmacon/GE (GIPZ Lentiviral Human EMCN shRNA: cat #: VGH5518-200276281 2; TRC Lentiviral Human EMCN shRNA: cat #: RHS3979-201850363; TRIPZ Inducible Lentiviral Human EMCN shRNA cat #: RHS4696-200681060).

Expression of shRNA in cells can be obtained by delivery of plasmids or through viral or bacterial vectors. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome (e.g., adeno-associated viruses (AAVs), adenoviruses, and lentiviruses). Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically.

Exemplary Endomucin shRNA (h) lentiviral particle includes, but is not limited to, Endomucin shRNA (h) lentiviral particle obtained from Santa Cruz Biotechnology, Inc. (Cat. No. sc-43156-V) and Dharmacon/GE (Cat No.: VGH5526).

In embodiments, EMCN inhibitors provided herein are EMCN-specific antibody or fragment thereof. In embodiments, the EMCN-specific antibody or fragment thereof is an antagonist antibody or fragment thereof. In embodiments, an EMCN-specific antibody described herein targets and binds to an extracellular domain (e.g., residues 19-190 of SEQ ID NO: 2) of EMCN. In embodiments, an EMCN-specific antibody described herein targets and binds to a fragment (e.g., any 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, or 165 residues) of an extracellular domain (e.g., residues 19-190 of SEQ ID NO: 2) of EMCN. Exemplary amino acid fragments of an extracellular domain include those that comprise the extracellular domain of EMCN-1, i.e., amino acids 19-190 (e.g., amino acids 19-190 of SEQ ID NO: 2). For example, a fragment of EMCN-1 comprises amino acids 19-100, 30-150, or 70-181; amino acids 70-89; or amino acids 173-181 of full length EMCN-1 (e.g., SEQ ID NO: 2).

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_ab$, $F_ab'$ and F(ab')2 fragments, an $F_ab$ expression library, single-chain antibody molecules (e.g., scFv), and multispecific antibodies formed from antibody fragments. By "specifically bind" or "immunoreacts with" is meant that the antibody reacts with one or more antigenic determinants of the desired antigen and does not react (i.e., bind) with other polypeptides or binds at much lower affinity ($K_d>10^{-6}$) with other polypeptides.

An "antibody fragment" refers to a molecule other than an intact antibody that comprises a portion of an intact antibody that binds the antigen to which the intact antibody binds. The terms "full length antibody," "intact antibody," and "whole antibody" are used herein interchangeably to refer to an antibody having a structure substantially similar to a native antibody structure or having heavy chains that contain an Fc region.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

In general, antibody molecules obtained from humans relate to any of the classes IgG, IgM, IgA, IgE and IgD, which differ from one another by the nature of the heavy chain present in the molecule. Certain classes have sub-classes as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art, "Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8 (10): 1057-1062 (1995). Briefly, these antibodies comprise a pair of tandem segments which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the term "epitope" includes any protein determinant capable of specific binding to an antibody, an antibody fragment, or a T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM; preferably $\leq 100$ nM and most preferably $\leq 10$ nM.

Antibodies can be produced according to any method known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press) Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples, the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In various examples the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies [e.g., Cole et al. 1985. Monoclonal Antibodies and Cancer Therapy Liss; Boerner et al. 1991. J. Immunol. 147(1):86-95]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368: 812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

In some embodiments, an intrabody is used to inhibit EMCN. An "intrabody" (from intracellular and antibody) is an antibody that works within the cell to bind to an intracellular antigen. Intrabodies typically lack disulfide bonds and are capable of modulating the expression or activity of target genes through their specific binding activity. Intrabodies include single domain fragments such as isolated VH and VL domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions. In various embodiments, the intrabody is expressed within a target cell, e.g., by a viral or plasmid expression vector that has been introduced into the target cell. An intrabody may remain in the cytoplasm, or it may have a nuclear localization signal, or it may undergo cotranslational translocation across the membrane into the lumen of the endoplasmic reticulum, provided that it is retained in that compartment through a KDEL sequence. Because antibodies ordinarily are designed to be secreted from the cell, intrabodies require special alterations, including the use of single-chain antibodies (scFvs), modification of immunoglobulin VL domains for hyperstability, selection of antibodies resistant to the more reducing intracellular environment, or expression as a fusion protein with maltose binding protein or other stable intracellular proteins. Non-limiting aspects of intrabodies are described, e.g., in U.S. Pat. No. 9,133,269; U.S. Patent Application Publication No. 2006/0034834; Chen et al. (1994) Human gene therapy 5 (5): 595-601; and Shaki-Loewenstein et al. (2005) Journal of immunological methods 303 (1-2): 19-39, the entire contents of each of which are incorporated herein by reference.

Exemplary antibodies against EMCN include, but are not limited to, antibodies obtained from LifeSpan BioSciences, Inc. (e.g., Cat Nos. LS-B10754; LS-C201493), ThermoFisher Scientific (Cambridge, Mass., USA) (e.g., Cat Nos. PA5-21395, PA5-42745, PA5-52229), and Antibodies-online. (e.g., Cat Nos. ABIN2782254, ABIN1385912, ABIN2157259).

In embodiments, EMCN inhibitors provided herein are small molecule inhibitors.

In embodiments, EMCN inhibitors provided herein are gene silencing systems, such as, clustered regularly interspaced short palindromic repeats (CRISPR). The CRISPR/Cas system is a prokaryotic immune system that confers resistance to foreign genetic elements such as those present within plasmids and phages that provides a form of acquired immunity. RNA harboring the spacer sequence helps Cas proteins recognize and cut exogenous DNA. The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule.

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) may generated in four sequential steps. First, two non-coding RNAs, the pre-crRNA array and tracrRNA, may be transcribed from the CRISPR locus. Second, tracrRNA may hybridize to the direct repeats of pre-crRNA, which is then processed into mature crRNAs containing individual spacer sequences. Third, the mature crRNA:tracrRNA complex may direct Cas9 to the DNA target consisting of the protospacer and the corresponding PAM via heteroduplex formation between the spacer region of the crRNA and the protospacer DNA. Finally, Cas9 may mediate cleavage of target DNA upstream of PAM to create a DSB within the protospacer.

The term "RNA-guided DNA endonuclease" and the like refer, in the usual and customary sense, to an enzyme that cleave a phosphodiester bond within a DNA polynucleotide chain, wherein the recognition of the phosphodiester bond is facilitated by a separate RNA sequence (for example, a single guide RNA).

The terms "single guide RNA," "single guide RNA sequence," "chimeric RNA," "chimeric guide RNA," "guide RNA", and "synthetic guide RNA" are used interchangeably and refer to the polynucleotide sequence including the crRNA sequence and optionally the tracrRNA sequence. The crRNA sequence includes a guide sequence (i.e., "guide" or "spacer") and a tracr mate sequence (i.e., direct repeat(s)". The term "guide sequence" refers to the sequence that specifies the target site.

In general, a guide sequence is any polynucleotide sequence having sufficient complementarity with a target polynucleotide sequence to hybridize with the target sequence (i.e., a mitochondrial DNA target sequence) and direct sequence-specific binding of a CRISPR complex to the target sequence (i.e., the mitochondrial DNA target sequence). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In general, a tracr mate sequence includes any sequence that has sufficient complementarity with a tracr sequence (i.e., a tracrRNA sequence) to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin.

Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. Where the tracrRNA sequence is less than 100 (99 or less) nucleotides in length the sequence is one of 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length.

Exemplary CRISPR system designed for EMCN can be obtained from, but is not limited to, Dharmacon/GE (Edit-R Predesigned Lentiviral Human EMCN sgRNA: cat #: GSGH11838-246537719; Edit-R Human EMCN crRNA: cat #: CM-015860-05-0002).

Dosages, formulations, dosage volumes, regimens, and methods for administering an EMCA inhibitor may vary. Thus, minimum and maximum effective dosages vary depending on the method of administration.

"Administering" an inhibitor described herein can be effected or performed using any of the various methods and delivery systems known to those skilled in the art. The administering can be, for example, intravenous, oral, ocular (e.g., subconjunctival, intravitreal, retrobulbar, or intracameral), intramuscular, intravascular, intra-arterial, intracoronary, intramyocardial, intraperitoneal, subcutaneous, inhaled, or intrathecal. Other non-limiting examples include topical administration, or coating of a device to be placed within the subject. In embodiments, administration is effected by injection or via a topical administration.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Pharmaceutical formulations adapted for topical administration may be formulated as aqueous solutions, ointments, creams, suspensions, lotions, powders, solutions, pastes, gels, sprays, aerosols, liposomes, microcapsules, microspheres, or oils.

In embodiments, compositions described herein include an EMCN inhibitor and a carrier or excipient suitable for administration to ocular tissue. Such carriers and excipients are suitable for administration to ocular tissue (e.g., sclera, lens, iris, cornea, uvea, retina, macula, or vitreous tissue) without undue adverse side effects (such as toxicity, irritation, and allergic response) commensurate with a reasonable benefit/risk ratio.

Pharmaceutical formulations adapted for topical administrations to the eye include eye drops where an EMCN inhibitor is dissolved or suspended in a suitable carrier, especially an aqueous solvent. Formulations to be administered to the eye will have ophthalmically compatible pH and osmolality. The term "ophthalmically acceptable vehicle" means a pharmaceutical composition having physical properties (e.g., pH and/or osmolality) that are physiologically compatible with ophthalmic tissues.

In some embodiments, an ophthalmic composition of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

In various embodiments, the ophthalmic formulations of the present invention may be in the form of liquid, solid or semisolid dosage form. The ophthalmic formulations of the present invention may comprise, depending on the final dosage form, suitable ophthalmically acceptable excipients. In embodiments, the ophthalmic formulations are formulated to maintain a physiologically tolerable pH range. In embodiments, the pH range of the ophthalmic formulation is in the range of from about 5 to about 9. In embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

The injection can be prepared by selecting and using an isotonicifier, a buffering agent, a surfactant, a thickener, etc., depending on necessity. The isotonicifier may be mentioned, for example, sodium chloride, etc. The buffering agent may be mentioned, for example, sodium phosphate, etc. The surfactant may be mentioned, for example, polyoxyethylene sorbitan monooleate, etc. The thickener may be mentioned, for example, methyl cellulose, etc.

The eye drop can be prepared by selecting and using an isotonicifier, a buffering agent, a surfactant, a stabilizer, an antiseptic, etc., depending on necessity, and a pH of which may be within the range acceptable for an ophthalmic preparation, it is usually preferred in the range of 4 to 8. The isotonicifier may be mentioned, for example, sodium chloride, concentrated glycerin, etc. The buffering agent may be mentioned, for example, sodium phosphate, sodium acetate, etc. The surfactant may be mentioned, polyoxyethylene sorbitan monooleate, polyoxyl 40 stearate, polyoxyethylene hardened castor oil, etc. The stabilizer may be mentioned, for example, sodium citrate, sodium edetate, etc. The antiseptic may be mentioned, for example, benzalkonium chloride, paraben, etc.

The ophthalmic ointment can be prepared by using a base generally used such as white petrolatum, liquid paraffin, etc.

The intercalating agent can be prepared by pulverizing and mixing a biodegradable polymer, for example, hydroxypropyl cellulose, hydroxypropylmethyl cellulose, carboxyvinyl polymer, polyacrylic acid, etc., with the present compound, and compression-molding the powder, and if necessary, an excipient, a binder, a stabilizer and/or a pH adjuster may be used.

One or more ophthalmically acceptable pH adjusting agents and/or buffering agents can be included in a composition of the invention, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g., poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition, and polymeric coatings that will enhance drug diffusion, erosion, dissolution, and osmosis.

Formulations for drug delivery using ocular devices may combine one or more active agents and adjuvants appropriate for the indicated route of administration. For example, an EMCN inhibitor (optionally with another agent) may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D,L-lactide-co-glycolide), poly (glycolide), poly (hydroxybutyrate), poly (alkylcarbonate) and poly (orthoesters), and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3; 57:1595-639 (2005), the entire content of which is incorporated herein by reference.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; 6,699,493; and 8,293,210, the entire contents of each of which are incorporated herein by reference.

The implants may be monolithic, i.e. having the active agent (e.g., an EMCN inhibitor) or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including an EMCN inhibitor, may be distributed in a non-homogenous pattern in the matrix. For example, the implant may include a portion that has a greater concentration of an EMCN inhibitor relative to a second portion of the implant.

The intraocular implants disclosed herein may have a size of between about 5 um and about 2 mm, or between about 10 um and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 ug, more preferably about 500-1000 ug. For example, an implant may be about 500 ug, or about 1000 ug. For non-human subject, the dimensions and total weight of the implant(s) may be larger or smaller, depending on the type of subject. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques, and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm Spheres may be in the range of 0.5 u.m to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Microspheres for ocular delivery are described, for example, in U.S. Pat. Nos. 5,837,226; 5,731,005; 5,641,750; 7,354,574; and U.S. Pub. No. 2008-0131484, the entire contents of each of which are incorporated herein by reference.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. Nos. 4,704,295; 4, 556,552; 4,309, 404; and 4,309,406, the entire contents of each of which are incorporated herein by reference.

Methods of Use

Also provided herein are methods for reducing neovascularization in an ocular tissue. The methods include contacting an ocular tissue in a subject in need thereof with an inhibitor of endomucin expression or activity (i.e., an EMCN inhibitor described herein), provided herein. An ocular tissue can include sclera, lens, iris, cornea, uvea, retina, macula, or vitreous tissue.

For example, the inhibitor is administered to a subject suffering from or at risk of developing diabetic retinopathy (DR), age-related macular degeneration (AMD), retinopathy of prematurity (ROP), or ischemic retinal vein occlusion (IRVO). In some examples, the inhibitor is administered via injection, e.g., intravitreally, for a period of time, e.g., daily, monthly, every 4-6 weeks, or at prescribed intervals until clinical symptoms are improved or resolved. In other examples, the inhibitor is administered topically.

Subjects to be treated have been diagnosed with aberrant angiogenesis in the eye. For example, the subject is an infant such as a premature baby that has been exposed to high concentrations of oxygen, e.g., a child that is suffering from or is at risk of developing oxygen-induced retinopathy and/or has been diagnosed as such. In other examples, the subject is an adult who has been diagnosed with, is suffering from, or is at risk of developing any of the disorders listed above. For example in the context of AMD, e.g., wet AMD, the subject is at least 50 years of age (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old). In embodiments, the subject is at least 65 years of age.

As used herein, a "monotherapy" is therapy that is administered to inhibit, treat, or prevent a disorder, such as aberrant angiogenesis (or a disease that includes aberrant angiogenesis such as PDR), without any other therapy that is used to treat the disorder. A monotherapy for treating a disorder may optionally be combined with another treatment that is used to ameliorate a symptom of the disorder while not being directed against the disorder, for example an analgesic compound, an antipyretic compound, and/or an anti-inflammatory compound (e.g., aspirin, ibuprofen, naproxen, or acetaminophen) may be administered concurrently with the monotherapy.

In various embodiments of the invention, a composition comprising an EMCN inhibitor may be administered only once or multiple times. For example, an EMCN inhibitor may be administered using a method disclosed herein at least about once, twice, three times, four times, five times, six times, or seven times per day, week, month, or year. In some embodiments, a composition comprising an EMCN inhibitor is administered once per month. In certain embodiments, the composition is administered once per month via intravitreal injection. In various embodiments, such as embodiments involving eye drops, a composition is self-administered.

For the treatment of an ocular disorder, an EMCN inhibitor (e.g., a pharmaceutical composition comprising an EMCN inhibitor) may be administered locally, e.g., as a topical eye drop, peri-ocular injection (e.g., sub-tenon), intraocular injection, intravitreal injection, retrobulbar injection, intraretinal injection, subretinal injection, subconjunctival injection, or using iontophoresis, or peri-ocular devices which can actively or passively deliver drug.

Sustained release of drug may be achieved by the use of technologies such as implants (e.g., solid implants) (which may or may not be bio-degradable) or bio-degradable polymeric matrices (e.g., micro-particles). These may be administered, e.g., peri-ocularly or intravitreally.

An administration dose of the compositions described herein may be optionally changed depending on a dosage form, severity of the symptoms, an age, a body weight or a volume of eye balls of a patient to be administered, and a judgment of a doctor, etc., and it can be generally administered to an adult person per a day of 0.01 to 10,000 mg, preferably 0.1 to 5,000 mg, more preferably 0.5 to 2,500 mg once or divided into several times, in the case of the injection, it can be generally administered to an adult person of 0.0001 to 2,000 mg once or divided into several times. In addition, in the case of the eye drops or the intercalating agent, it can be administered a material having a concentration of an active ingredient of 0.000001 to 10% (w/v), preferably 0.00001 to 1% (w/v), more preferably 0.0001 to 0.1% (w/v) once a day or divided into several times. Moreover, in the case of the plasters, the plaster containing 0.0001 to 2,000 mg can be patched to an adult person, and in the case of the preparation for intraocular implant, the preparation for intraocular implant containing 0.0001 to 2,000 mg can be implanted into eyes to an adult person.

Diabetic Retinopathy

Diabetic retinopathy is a condition that occurs in people who have diabetes. It causes progressive damage to the retina, which is the light-sensitive lining at the back of the eye. Diabetic retinopathy is a serious sight-threatening complication of diabetes. See, e.g., American Optometric Association, Diabetic Retinopathy, available from www.aoa.org/patients-and-public/eye-and-vision-problems/glossary-ofeye-and-vision-conditions/diabetic-retinopathy?sso=y, the entire contents of which are incorporated herein by reference.

Diabetes interferes with the body's ability to use and store sugar (glucose). The disease is characterized by too much sugar in the blood, which can cause damage throughout the body, including the eyes. Over time, diabetes damages the blood vessels in the retina. Diabetic retinopathy occurs when these tiny blood vessels leak blood and other fluids. This causes the retinal tissue to swell, resulting in cloudy or blurred vision. The condition usually affects both eyes. The longer a person has diabetes, the more likely they will develop diabetic retinopathy. If left untreated, diabetic retinopathy can cause blindness.

Symptoms of diabetic retinopathy include (i) seeing spots or floaters; (ii) blurred vision; (iii) having a dark or empty spot in the center of vision; and (iv) difficulty seeing well at night.

Often the early stages of diabetic retinopathy have no visual symptoms. Early detection and treatment can limit the potential for significant vision loss from diabetic retinopathy. In some embodiments, a subject with diabetes or early stage diabetic retinopathy is administered an EMCN inhibitor to halt, prevent, inhibit, or treat the progression of diabetic retinopathy. In certain embodiments, visual symptoms are delayed or prevented.

PDR is a more advanced form of the disease. At this stage, new fragile blood vessels can begin to grow in the retina and into the vitreous (the gel-like fluid that fills the back of the eye). The new blood vessels may leak blood into the vitreous, clouding vision.

Without wishing to be bound by any scientific theory, diabetic retinopathy results from the damage diabetes causes to the small blood vessels located in the retina. These damaged blood vessels can cause vision loss. For example, fluid can leak into the macula, the area of the retina responsible for clear central vision. Although small, the macula is the part of the retina that allows us to see colors and fine detail. The fluid causes the macula to swell, resulting in blurred vision. In an attempt to improve blood circulation in the retina, new blood vessels may form on its surface. These fragile, abnormal blood vessels can leak blood into the back of the eye and block vision.

Diabetic retinopathy is classified into two types:

(1) Non-proliferative diabetic retinopathy (NPDR) is the early stage of the disease in which symptoms will be mild or nonexistent. In NPDR, the blood vessels in the retina are weakened. Tiny bulges in the blood vessels, called microaneurysms, may leak fluid into the retina. This leakage may lead to swelling of the macula.

(2) PDR is the more advanced form of the disease. At this stage, circulation problems deprive the retina of oxygen. As a result new, fragile blood vessels can begin to grow in the retina and into the vitreous, the gel-like fluid that fills the back of the eye. The new blood vessels may leak blood into the vitreous, clouding vision.

Both NPDR and PDR may also result in macular edema. Embodiments of the present subject matter relate to the reduction of macular edema in subjects with diabetic retinopathy.

Other complications of PDR include detachment of the retina due to scar tissue formation and the development of neovascular glaucoma. Glaucoma is an eye disease in which there is progressive damage to the optic nerve. In PDR, new blood vessels grow into the area of the eye that drains fluid from the eye. This greatly raises the eye pressure, which damages the optic nerve. If left untreated, PDR can cause severe vision loss and even blindness.

In some embodiments, a subject who is at risk of developing diabetic retinopathy is administered an EMCN inhibitor to delay, prevent, or ameliorate the onset of the disease (e.g., NPDR and/or PDR and/or macular edema). Risk factors for diabetic retinopathy include:

(i) Diabetes. People with type 1 or type 2 diabetes are at risk for developing diabetic retinopathy. The longer a person has diabetes, the more likely he or she is to develop diabetic retinopathy, particularly if the diabetes is poorly controlled.

(ii) Race. Hispanics and African Americans are at greater risk for developing diabetic retinopathy.

(iii) Medical conditions. People with other medical conditions, such as high blood pressure and high cholesterol, are at greater risk.

(iv) Pregnancy. Pregnant women face a higher risk for developing diabetes and diabetic retinopathy. If a woman develops gestational diabetes, she has a higher risk of developing diabetes as she ages.

Non-limiting examples of methods for diagnosing diabetic retinopathy include dilated eye examination, visual acuity tests, slit-lamp examination, fluorescein angiography, optical coherence tomography (OCT), and ultrasound. See, e.g., Kierstan Boyd (2013) "Diabetic Retinopathy Diagnosis" American Academyof Ophthamology (available at www.aao.org/eye-health/diseases/diabetic-retinopathy-diagnosis); and Mayo Clinic (2015) "Diabetic retinopathy, Tests and diagnosis" (available at www.mayoclinic.org/diseases-conditions/diabetic-retinopathy/basics/tests-diagnosis/con-20023311) the entire content of each of which is hereby incorporated by reference.

Any symptom, type, or stage of diabetic retinopathy may be inhibited, treated, or prevented using methods and compositions disclosed herein.

Retinopathy of Prematurity

Retinopathy of prematurity (ROP) is a potentially blinding eye disorder that primarily affects premature infants weighing about 2¾ pounds (1250 grams) or less that are born before 31 weeks of gestation (a full-term pregnancy has a gestation of 38-42 weeks). The smaller a baby is at birth, the more likely that baby is to develop ROP. This disorder, which usually develops in both eyes, is one of the most common causes of visual loss in childhood and can lead to lifelong vision impairment and blindness. See, e.g., National Eye Institute, Facts About Retinopathy of Prematurity (ROP), available from nei.nih.gov/health/rop/rop, the entire contents of which are incorporated herein by reference.

Today, with advances in neonatal care, smaller and more premature infants are being saved. These infants are at a much higher risk for ROP. Not all babies who are premature develop ROP. There are approximately 3.9 million infants born in the U.S. each year; of those, about 28,000 weigh 2¾ pounds or less. About 14,000-16,000 of these infants are affected by some degree of ROP. The disease improves and leaves no permanent damage in milder cases of ROP. About 90 percent of all infants with ROP are in the milder category and do not need treatment. However, infants with more severe disease can develop impaired vision or even blindness. About 1,100-1,500 infants annually develop ROP that is severe enough to require medical treatment. About 400-600 infants each year in the US become legally blind from ROP.

ROP is classified in five stages, ranging from mild (stage I) to severe (stage V):

Stage I—Mildly abnormal blood vessel growth. Many children who develop stage I improve with no treatment and eventually develop normal vision. The disease resolves on its own without further progression.

Stage II—Moderately abnormal blood vessel growth. Many children who develop stage II improve with no treatment and eventually develop normal vision. The disease resolves on its own without further progression.

Stage III—Severely abnormal blood vessel growth. The abnormal blood vessels grow toward the center of the eye instead of following their normal growth pattern along the surface of the retina. Some infants who develop stage III improve with no treatment and eventually develop normal vision. However, when infants have a certain degree of Stage III and "plus disease" develops, treatment is considered. "Plus disease" means that the blood vessels of the retina have become enlarged and twisted, indicating a worsening of the disease. Treatment at this point has a good chance of preventing retinal detachment.

Stage IV—Partially detached retina. Traction from the scar produced by bleeding, abnormal vessels pulls the retina away from the wall of the eye.

Stage V—Completely detached retina and the end stage of the disease. If the eye is left alone at this stage, the baby can have severe visual impairment and even blindness.

Most babies who develop ROP have stages I or II. However, in a small number of babies, ROP worsens, sometimes very rapidly. Untreated ROP threatens to destroy vision.

ROP occurs when abnormal blood vessels grow and spread throughout the retina, the tissue that lines the back of the eye. These abnormal blood vessels are fragile and can leak, scarring the retina and pulling it out of position. This causes a retinal detachment. Retinal detachment is the main cause of visual impairment and blindness in ROP.

Without wishing to be bound by any scientific theory, several complex factors may be responsible for the development of ROP. The eye starts to develop at about 16 weeks of pregnancy, when the blood vessels of the retina begin to form at the optic nerve in the back of the eye. The blood vessels grow gradually toward the edges of the developing retina, supplying oxygen and nutrients. During the last 12 weeks of a pregnancy, the eye develops rapidly. When a baby is born full-term, the retinal blood vessel growth is mostly complete (the retina usually finishes growing a few weeks to a month after birth). But if a baby is born prematurely, before these blood vessels have reached the edges of the retina, normal vessel growth may stop. The edges of the retina (the periphery) may not get enough oxygen and nutrients. The periphery of the retina may then send out signals to other areas of the retina for nourishment. As a result, new abnormal vessels begin to grow. These new blood vessels are fragile and weak and can bleed, leading to retinal scarring. When these scars shrink, they pull on the retina, causing it to detach from the back of the eye.

A non-limiting example of a method for diagnosing ROP includes dilated eye examination. See, e.g., American Association for Pediatric Ophthalmology and Strabismus (2016) *Retinopathy of Prematurity* (available at aapos.org/terms/conditions/94), the entire content of which is incorporated herein by reference.

Aspects of the present invention relate to inhibiting, preventing, or treating the onset of or the progression of a ROP in a premature infant. Any symptom or stage of ROP may be inhibited, treated, or prevented using methods and compositions disclosed herein.

Age-Related Macular Degeneration

Age-related macular degeneration (AMD) is an eye disease that is a leading cause of vision loss in older people in developed countries. The vision loss usually becomes noticeable in a person's sixties or seventies and tends to worsen over time. See, e.g., the U.S. National Library of Medicine Genetics Home Reference, Age-Related Macular Degeneration, available at ghr.nlm nih.gov/condition/age-related-macular-degeneration, the entire contents of which are incorporated herein by reference.

Age-related macular degeneration mainly affects central vision, which is needed for detailed tasks such as reading, driving, and recognizing faces. The vision loss in this condition results from a gradual deterioration of light-sensing cells in the tissue at the back of the eye that detects light and color (the retina). Specifically, age-related macular degeneration affects a small area near the center of the retina, called the macula, which is responsible for central vision. Side (peripheral) vision and night vision are generally not affected.

Researchers have described two major types of age-related macular degeneration, known as the dry form and the wet form. The dry form is much more common, accounting for 85 to 90 percent of all cases of AMD. It is characterized by a buildup of yellowish deposits called drusen beneath the retina and slowly progressive vision loss. The condition typically affects vision in both eyes, although vision loss often occurs in one eye before the other.

The wet form of age-related macular degeneration is associated with severe vision loss that can worsen rapidly. This form of the condition is characterized by the growth of abnormal, fragile blood vessels underneath the macula. These vessels leak blood and fluid, which damages the macula and makes central vision appear blurry and distorted.

In some embodiments, a subject who is at risk of developing AMD is administered an EMCN inhibitor to delay, prevent, or ameliorate the onset of AMD. AMD results from a combination of genetic and environmental factors. Many of these factors have been identified, but some remain unknown.

Researchers have considered changes in many genes as possible risk factors for AMD. The best-studied of these genes are involved in a part of the body's immune response known as the complement system. This system is a group of proteins that work together to destroy foreign invaders (such as bacteria and viruses), trigger inflammation, and remove debris from cells and tissues. Genetic changes in and around several complement system genes, including the complement factor H (CFH) gene, contribute to a person's risk of developing AMD. It is unclear how these genetic changes are related to the retinal damage and vision loss characteristic of this condition.

Changes on the long (q) arm of chromosome 10 in a region known as 10q26 are also associated with an increased risk of AMD. The 10q26 region contains two genes of interest, age-related maculopathy susceptibility 2 (ARMS2) and HtrA Serine Peptidase 1 (HTRA1). Changes in both genes have been studied as possible risk factors for the disease. However, because the two genes are so close together, it is difficult to tell which gene is associated with AMD risk, or whether increased risk results from variations in both genes. An estimated 15 to 20 percent of people with AMD have at least one first-degree relative (such as a sibling) with the condition.

Other genes that are associated with AMD include genes involved in transporting and processing high-density lipoprotein (HDL) and genes that have been associated with other forms of macular disease.

Nongenetic factors also contribute to the risk of age-related macular degeneration. Age appears to be the most important risk factor; the chance of developing the condition increases significantly as a person gets older. Smoking is another established risk factor for AMD.

Aspects of the present subject matter relate to administering an EMCN inhibitor to a subject who is diagnosed with or determined to be at risk of developing AMD. Subjects at risk of developing AMD include subjects with high blood pressure, heart disease, a high-fat diet or a diet that is low in certain nutrients (such as antioxidants and zinc), obesity, repeated and/or prolonged exposure to ultraviolet (UV) rays from sunlight, and/or who smoke or have smoked for at least about 1, 5, 10, or more years, and/or who are at least about 50, 55, 60, 65, 70, 75, 80, 85, or 90 years old. Subjects at risk of developing AMD and/or a symptom or complication thereof also include subjects with at least 1 or 2 grandparents, parents, or siblings who suffer from AMD, and/or the symptom or complication thereof.

Non-limiting examples of methods for diagnosing AMD include examination of the back of the eye (e.g., with an ophthalmoscope), tests for defects in the center of a subject's vision, fluorescein angiography, indocyanine green angiography, and optical coherence tomography. See, e.g., Mayo Clinic (2015) "Dry Macular Degeneration" (available at www.mayoclinic.org/diseases-conditions/dry-macular-degeneration/diagnosis-treatment/diagnosis/dxc-20165013); Mayo Clinic (2015) "Wet macular degeneration" (available at www.mayoclinic.org/diseases-conditions/wet-macular-degeneration/diagnosis-treatment/diagnosis/dxc-20164284), the entire contents of each of which are incorporated herein by reference.

Any symptom, type, or stage of AMD may be inhibited, treated, or prevented using methods and compositions disclosed herein.

Retinal Vein Occlusion

Retinal vein occlusion (RVO) is a blockage of the small veins that carry blood away from the retina. Retinal vein occlusion is most often caused by hardening of the arteries (atherosclerosis) and the formation of a blood clot. Blockage of smaller veins (branch veins or BRVO) in the retina often occurs in places where retinal arteries that have been thickened or hardened by atherosclerosis cross over and place pressure on a retinal vein. See, e.g., U.S. National Library of Medicine, Retinal vein occlusion, available at www nlm nih.gov/medlineplus/ency/article/007330.htm, the entire contents of which are incorporated herein by reference.

Risk factors for retinal vein occlusion include: (i) atherosclerosis; (ii) diabetes; (iii) high blood pressure (hypertension; e.g., a systolic pressure of at least 140 mmHg or a diastolic pressure of at least 90 mmHg); and (iv) other eye conditions, such as glaucoma, macular edema, or vitreous hemorrhage. The risk of these disorders increases with age, therefore retinal vein occlusion most often affects older people.

Blockage of retinal veins may cause other eye problems, including: (i) glaucoma (high pressure in the eye), caused by new, abnormal blood vessels growing in the front part of the eye; (ii) neovascularization (RVO can cause the retina to develop new, abnormal blood vessels, a condition called neovascularization. These new vessels may leak blood or fluid into the vitreous, the jelly-like substance that fills the inside of the eye. Small spots or clouds, called floaters, may appear in the field of vision. With severe neovascularization, the retina may detach from the back of the eye); (iii) macular edema, caused by the leakage of fluid in the retina; and (iv) neovascular glaucoma (New blood vessels in certain parts of the eye can cause pain and a dangerous increase in pressure inside the eye).

Non-limiting examples of methods for diagnosing RVO include optical coherence tomography, ophthalmoscopy, and fluorescein angiography. See, e.g., Cleveland Clinic (2015) "Retinal Vein Occlusion" (available at my.clevelandclinic.org/services/cole-eye/diseases-conditions/hic-retinal-vein-occlusion), the entire content of which is incorporated herein by reference.

Any symptom, type, or stage of retinal vein occlusion may be inhibited, treated, or prevented using methods and compositions disclosed herein.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Endomucin Plays a Role in Retinal Vascular Development and in VEGF-Induced Endothelial Cell Migration, Growth, and Morphogenesis Angiogenesis is central to both normal and pathologic processes. ECs express high levels of O-glycoproteins that are believed to play important roles in vascular development and stability. EMCN is a type I O-glycosylated, sialic-rich glycoprotein, specifically expressed by venous and capillary endothelium. Although ECs express high levels of EMCN, its role in vascular development has not been examined. A role for EMCN in angiogenesis was studied by modulating gene expression in vitro and in vivo. Postnatal day (P) four C57BL/6 mice were injected intravitreally with siEMCN or scramble siRNA (siCtrl). EMCN-specific target sequences include the following sequences (commercially available from Dharmacon/GE Healthcare);

```
ON-TARGETplus SMART pool siRNA J-015860-09 EMCN
Target Sequence:
                                         (SEQ ID NO: 4)
GCGUGAAGCUUCUUACCGU ON-TARGETplus SMART pool siRNA J-015860-10 EMCN
Target Sequence:
                                         (SEQ ID NO: 5)
AGGCAAUAAUUACGCUUAA ON-TARGETplus SMART pool siRNA J-015860-11 EMCN
Target Sequence:
                                         (SEQ ID NO: 6)
GGAAAAGUUGCACGUGUAU ON-TARGETplus SMART pool siRNA J-015860-12 EMCN
Target Sequence:
                                         (SEQ ID NO: 7)
CAUCAUUUCAAACGUAACA
```

Knockdown of EMCN mRNA was significant at 48 hrs after injection compared to siCtrl mice. A delay in radial expansion of the developing mouse vasculature was observed in siEMCN-injected P6 mice (51±2.2 vs. 69±1.8%, P<0.0001), accompanied by reduced vessel density (49±1.9 vs. 66±4.8%, P<0.01), branch point number (43±1.1 vs. 64±4.0 mm$^2$, P<0.0001), and tip cell number (18±0.6 vs. 28±2.1 mm, P<0.05) when compared to siCtrl mice. Knockdown of EMCN in human retinal ECs led to a reduction in VEGF-induced migration (22±1.3 vs. 59±2.7%, P<0.0001), proliferation (1.51×10$^4$±125.0 vs. 2.25×10$^4$±1500 cell/cm$^2$, P<0.05), and morphogenesis (7201±86 vs. 9157±273.0 mm, P<0.005) compared to siCtrl cells, without compromising cell survival. VEGF stimulation of siEMCN transfected ECs showed reduction in phospho-VEGFR2, phospho-ERK1/2 and phospho-Akt levels. Taken together, the data indicated a role for EMCN as an important regulator of angiogenesis.

Endomucin Plays a Role in Developmental Retinal Vascularization and in VEGF-Induced Endothelial Cell Migration, Growth, and Morphogenesis In Vitro Angiogenesis is complex and proceeds through several stages including migration, proliferation and morphogenesis of endothelial cells (EC). It is central to both normal and pathologic processes. Endomucin-1 (EMCN), a type I O-glycosylated sialic-rich glycoprotein and a component of the endothelial glycocalyx, is specifically expressed by venous and capillary endothelium. Although EC express high levels of EMCN, the role of EMCN in vascular development was unclear prior to the invention. Thus, the role of EMCN in angiogenesis was examined.

C57BL/6J mice were injected intravitreally with siEMCN or scrambled siRNA (siCtrl) at postnatal day four (P4). Two days after injection, retinas were flat-mounted and vascular radial expansion, vessel density, branch point number, and filopodia number were evaluated. In a series of in vitro studies aimed at elucidating mechanism, EMCN was knocked down in human retinal EC (HREC) by transfection with siEMCN. EC migration was assessed in a wound-healing assay, proliferation was determined by cell counting, and tube morphogenesis was examined using the collagen EC tube formation assay. Levels of apoptosis were evaluated by Annexin-V staining and quantified using the Muse analyzer. For all experiments, the siRNA knockdown efficiency was confirmed on mRNA and protein levels.

Knockdown of EMCN mRNA in the retina was significant at 48 and 72 hrs after intravitreal injection compared to siCtrl treatment. Delay in radial expansion of the developing mouse vasculature in siEMCN-injected P6 mice ($51 \pm 2.2\%$ vs. $69 \pm 1.8\%$, P<0.0001) was observed and was accompanied by reduced vessel density ($49 \pm 1.9\%$ vs. $66 \pm 4.8\%$, P<0.01), decreased branch point number ($43 \pm 1.1$ mm$^2$ vs. $64 \pm 4.0$ mm$^2$, P<0.0001), and reduced number of filopodia ($18 \pm 0.6$ mm vs. $28 \pm 2.1$ mm, P<0.05) when compared to siCtrl. Knockdown of EMCN in HREC led to a reduction in VEGF-induced migration ($22 \pm 1.3\%$ vs. $59 \pm 2.7\%$, P<0.0001), proliferation ($1.51 \times 10^4 \pm 125.0$ vs. $2.25 \times 10^4 \pm 1500$ cell/cm$^2$, P<0.05), and morphogenesis ($7201 \pm 86$ mm vs. $9157 \pm 273.0$ mm, P<0.005) compared to siCtrl-treated cells, without compromising cell survival. VEGF stimulation of siEMCN transfected ECs showed reduction in phospho-VEGFR2, phospho-ERK1/2 and phospho-Akt levels. The data establishes that EMCN is an important regulator of angiogenesis.

Role of EMCN in Retinal Neovascularization

Functional effects of EMCN in pathological retinal neovascularization were studied using a gain- and loss-of-function approach. The data described above and in the figures described below indicate that EMCN siRNA attenuates pathologic vessel proliferation and results in fewer neovascular tufts at P17, indicating decreased neovascularization with EMCN siRNA treatment compared to control eyes.

Inhibition and Overexpression o EMCN on Human Retinal Endothelial Cells

Figure 1B:
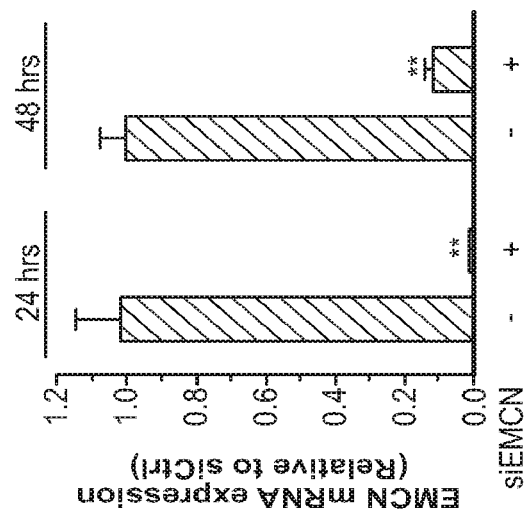
Figure 1C:
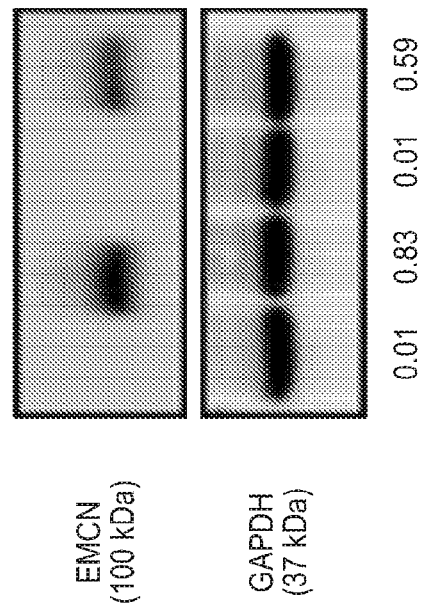
Figure 1D:
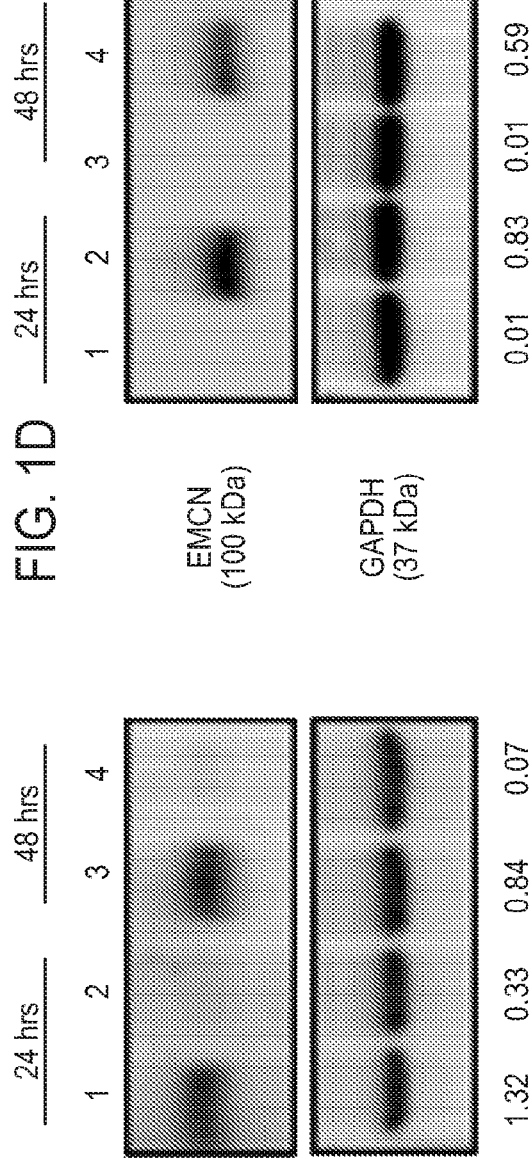

FIGS. 1A-1D show the effect of knockdown and overexpression of EMCN in treated human retinal EC (HREC). FIG. 1A: EMCN-siRNA resulted in 90% reduction at 24 hr and 48 hr in mRNA expression compared to non-targeting control siRNA (siCtrl). FIG. 1B: EMCN-siRNA led to a 90% suppression of EMCN protein at 24 and 48 hr. FIG. 1C and FIG. 1D: Exposure to AdEMCN resulted in a significant increase in EMCN mRNA (9-fold increase) and protein (10-fold increase) at 24 and 48 hr compared to control after infection. Results are representative from three independent experiments.P<0.01,*P<0.001 siEMCN vs siCtrl or AdEMCN vs AdGFP. Error bars represent SEM.

EMCN Regulates VEGF-Induced Endothelial Cell Migration

Figure 2E:
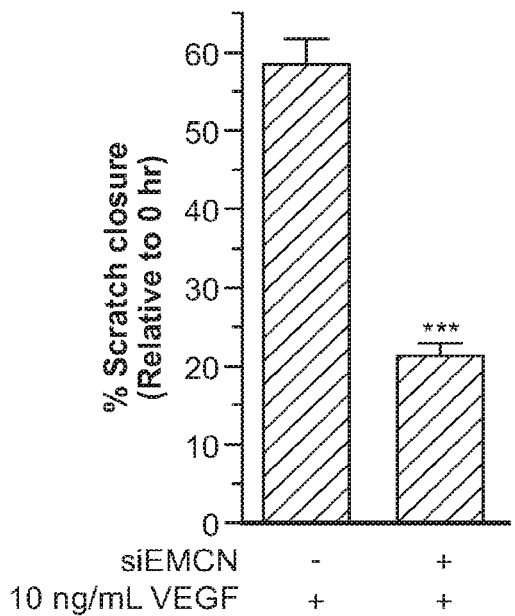
Figure 2F:
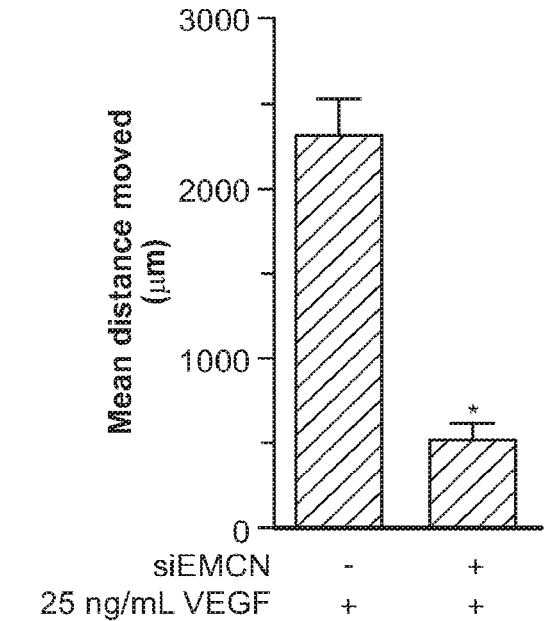
Figure 2G:
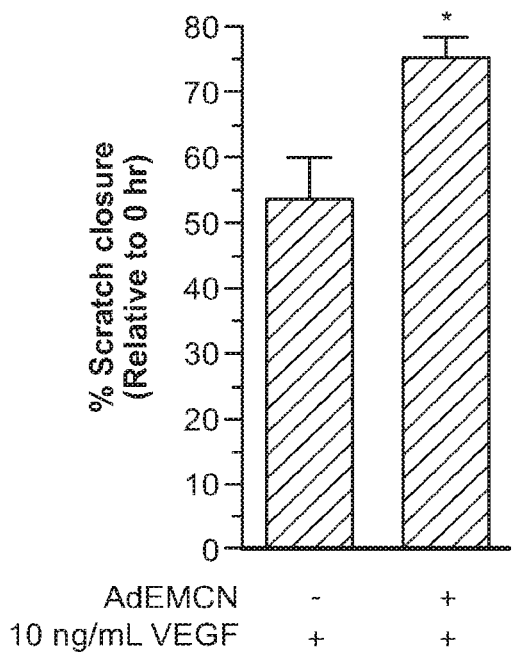
Figure 2H:
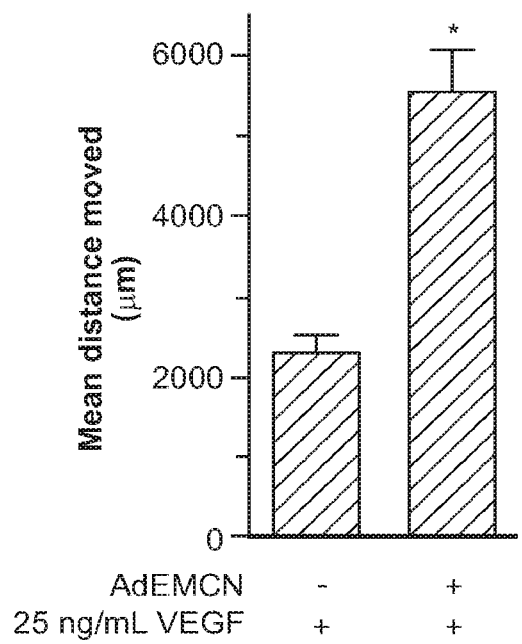

FIGS. 2A-2H show that EMCN regulates VEGF-induced endothelial cell migration. HRECs were transfected with siCtrl, siEMCN, or infected with AdGFP or AdEMCN and cell migration was measured by a wound assay FIG. 1A and FIG. 2C or an under-agarose assay FIG. 2B and FIG. 2D. FIG. 2A: Cells with reduced EMCN had reduced wound-closure (67% less than controls) at 10 hr post-wounding while AdEMCN infected cells exhibited a 1.4-fold increase in migration after 10 hrs when compared with AdGFP control cells (FIG. 2C). FIG. 2B: HREC in which EMCN was knocked down with siEMCN migrated up to 0.5 mm from the starting point while control cells (treated with siCtrl) migrated up to 2.3 mm FIG. 2D: The migration of AdEMCN infected cells In response to VEGF at 36 hr was increased 2.6-fold compared to that of AdGFP-infected control cells. Results are from four independent experiments in triplicate. *P<0.05, ***P<0.001 siEMCN vs siCtrl or AdEMCN vs AdGFP. Error bars represent SEM. Scale bar 500 μm.

EMCN Regulated VEGF-Stimulated Endothelial Cell Proliferation

Figure 3A:
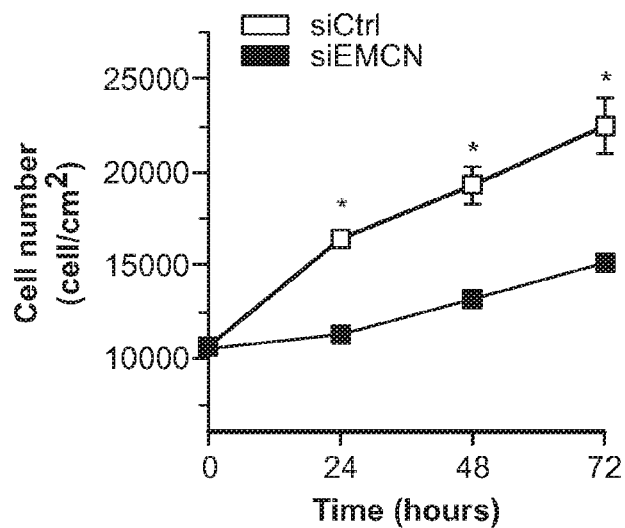
FIGS. 3A-3E. EMCN regulated VEGF-stimulated endothelial cell proliferation. Trypan blue exclusion assay was used to score cells under different conditions. Cell viability and growth were measured on cells with EMCN knockdown or control cells 24 hr after transfection.
Figure 3B:
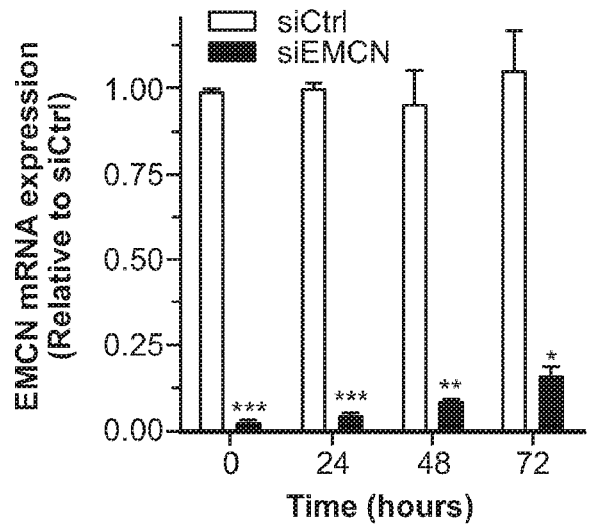
Figure 3C:
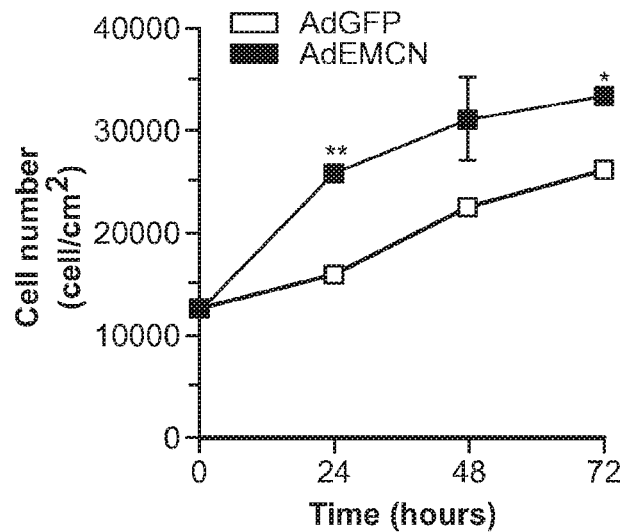
Figure 3D:
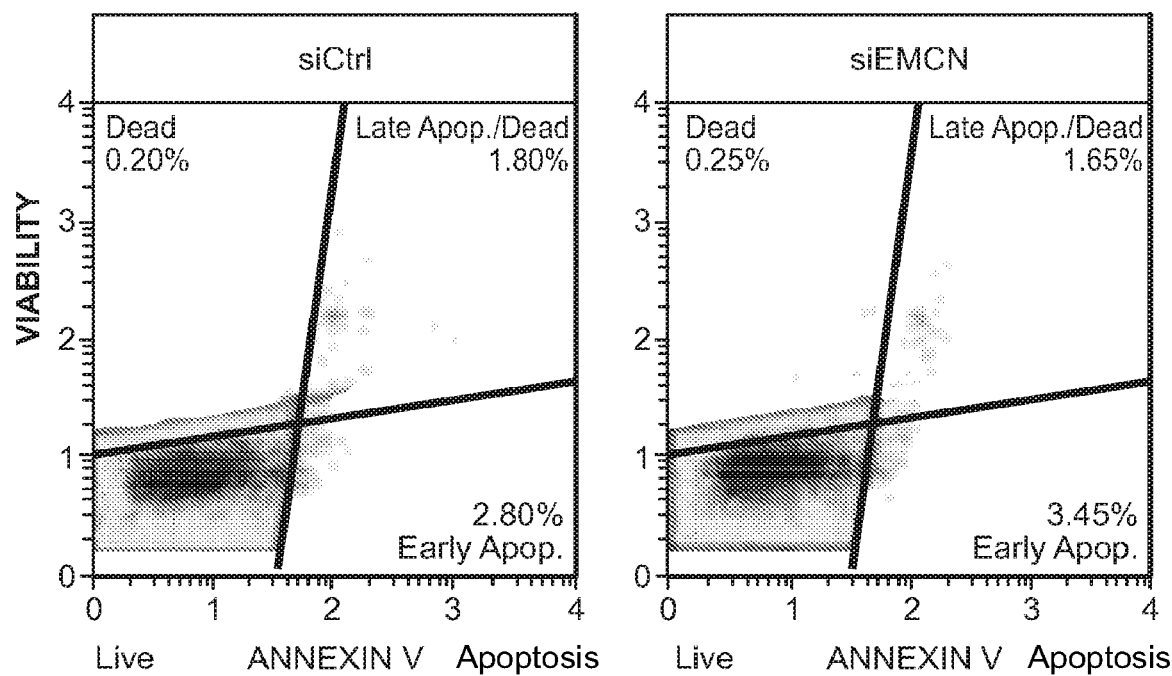
Figure 3E:
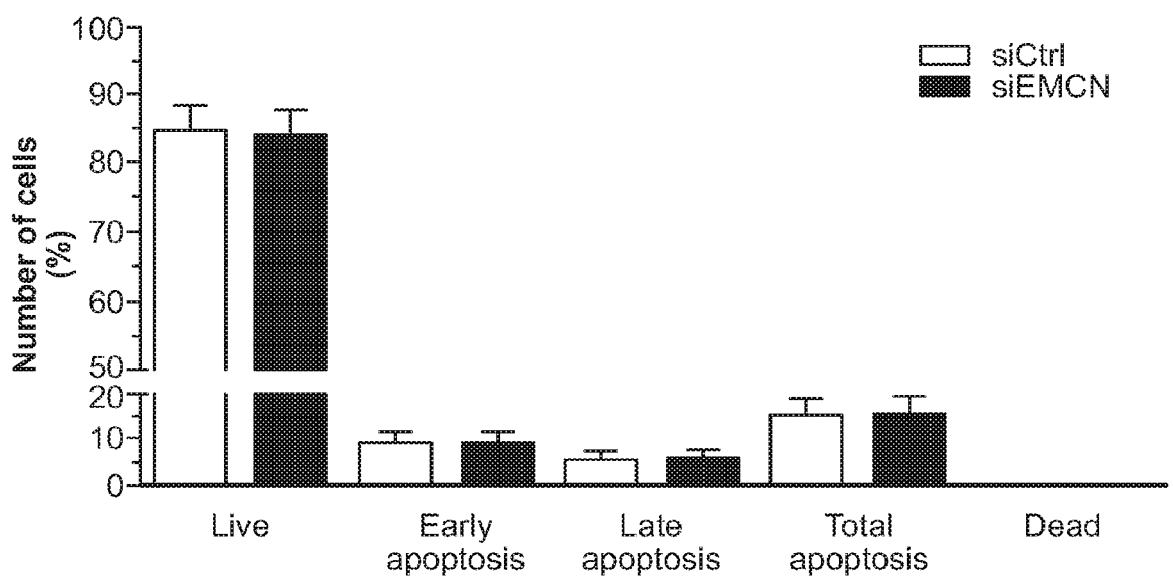

FIGS. 3A-3E demonstrate that EMCN regulated VEGF-stimulated endothelial cell proliferation. Trypan blue exclusion assay was used to score cells under different conditions. Cell viability and growth were measured on cells with EMCN knockdown or control cells 24 hr after transfection. FIG. 3A: In the presence of VEGF (10 ng/mL), the cells were viable and EMCN-deficient cells displayed a significant decrease in cell proliferation (a 50% decrease) compared to control cells. FIG. 3B: Reduced EMCN mRNA expression was confirmed at each time-point. FIG. 3C: Cells infected with AdEMCN resulted in an increase in cell proliferation compared to AdGFP cells. FIGS. 3D-3E: Cytofluorimetric analysis of annexin V in HRECs showed minimal or no change in total apoptotic events in EMCN-reduced cells compared with the control cells. Results are from three independent experiments in triplicate. *P<0.05, P<0.01, *P<0.001 siEMCN vs siCtrl or AdEMCN vs AdGFP. Error bars represent SEM.

EMCN Expression Modulates VEGF-Induced Tube Morphogenesis

FIGS. 4A-4D show data demonstrating that EMCN expression modulates VEGF-induced tube morphogenesis by HRECs. FIG. 4A and FIG. 4B: Results demonstrated that tube formation by EC with reduced EMCN was inhibited by approximately 22% and 18% in the absence or presence of VEGF after 6 hr, respectively. FIG. 4C and FIG. 4D Conversely, the morphogenic response of AdEMCN infected cells was more increased 1.4- and 1.3-fold increase over that observed in AdGFP control cells in the absence or presence of VEGF at 6 hr, respectively. Quantitative results are from three independent experiments. *P<0.05, ***P<0.001 siEMCN vs siCtrl or AdEMCN vs AdGFP; *P<0.05, **P<0.01 VEGF vs no VEGF. Error bars represent SEM. Scale bar 100 μm.

Loss of EMCN Results in Defective Retinal Vascular Development

Figure 5A:
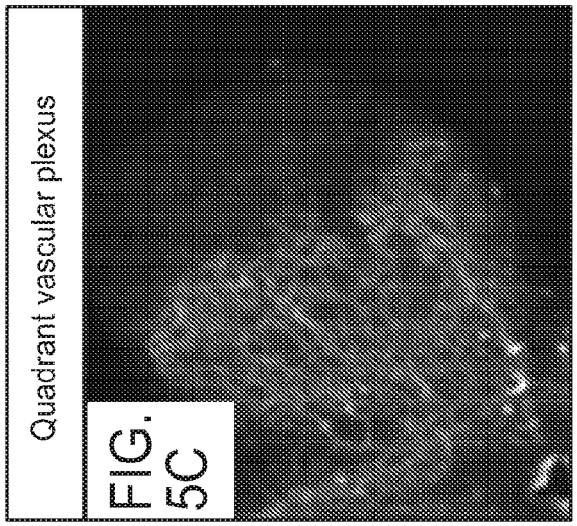
Figure 5B:
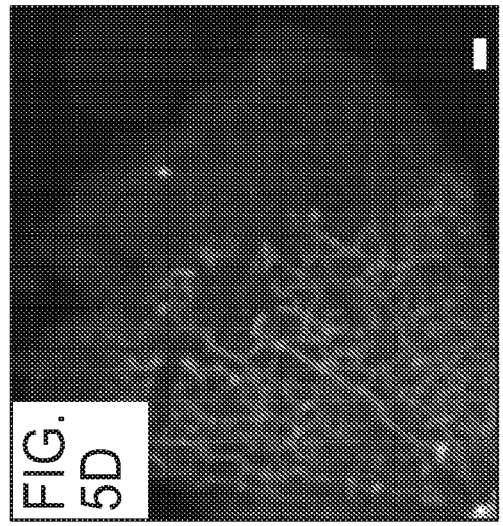
Figure 5C:
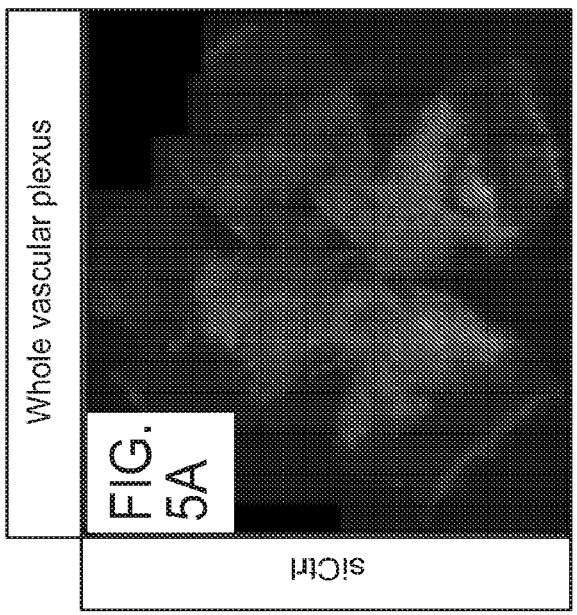
Figure 5D:
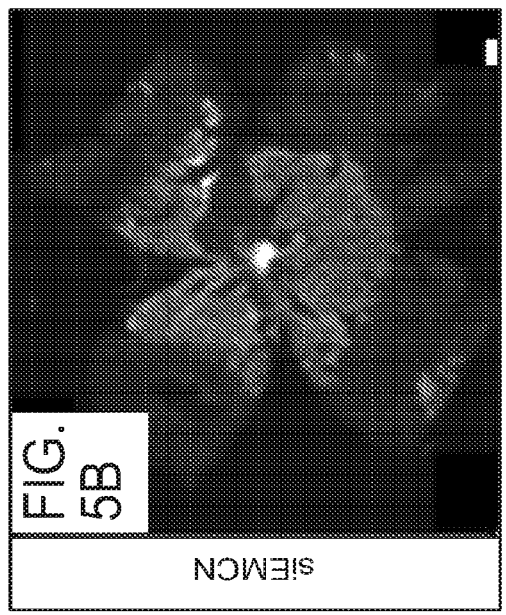
Figure 5I:
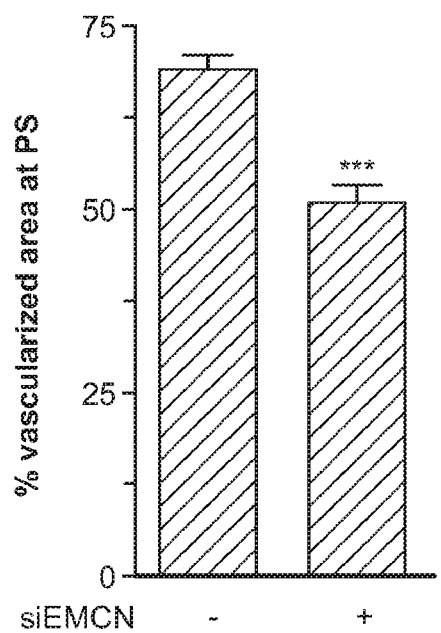
Figure 5J:
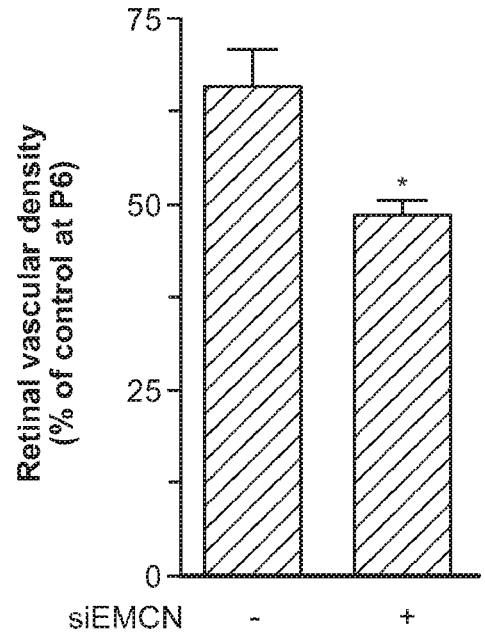
Figure 5K:
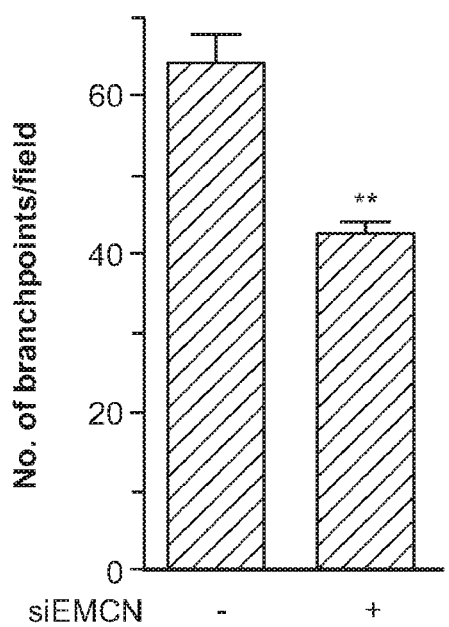
Figure 5L:
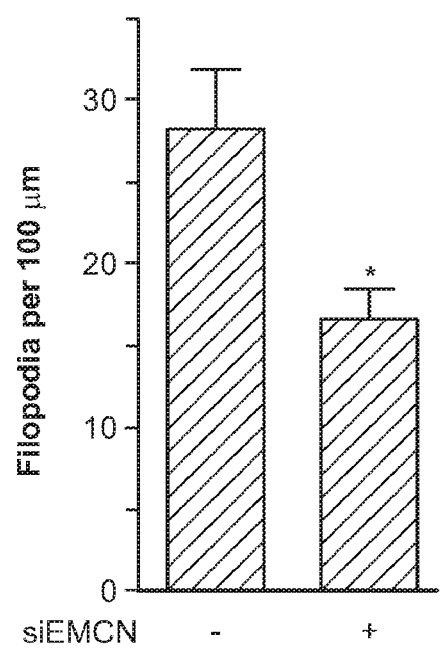
Figure 6A:
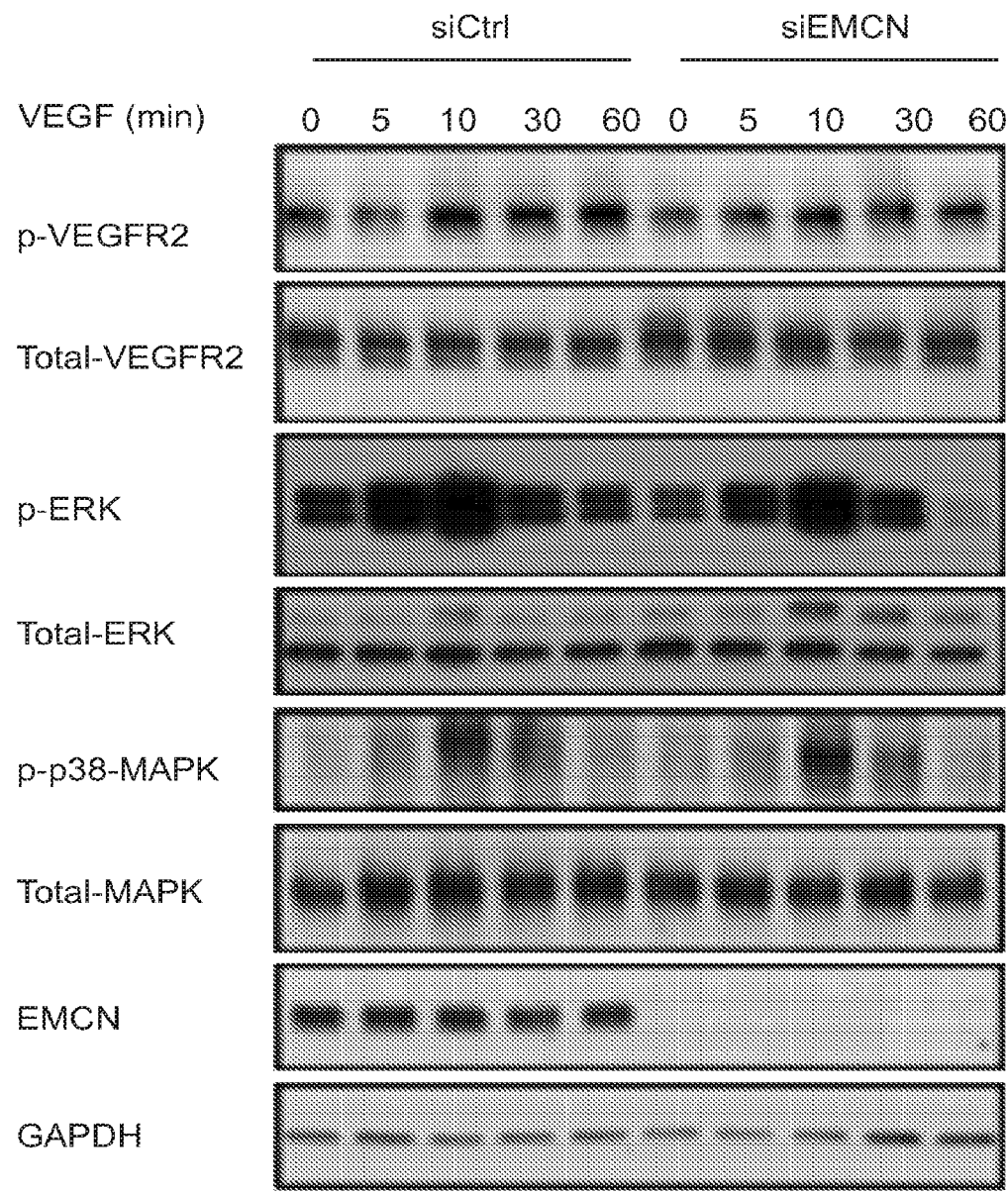
Figure 7A:
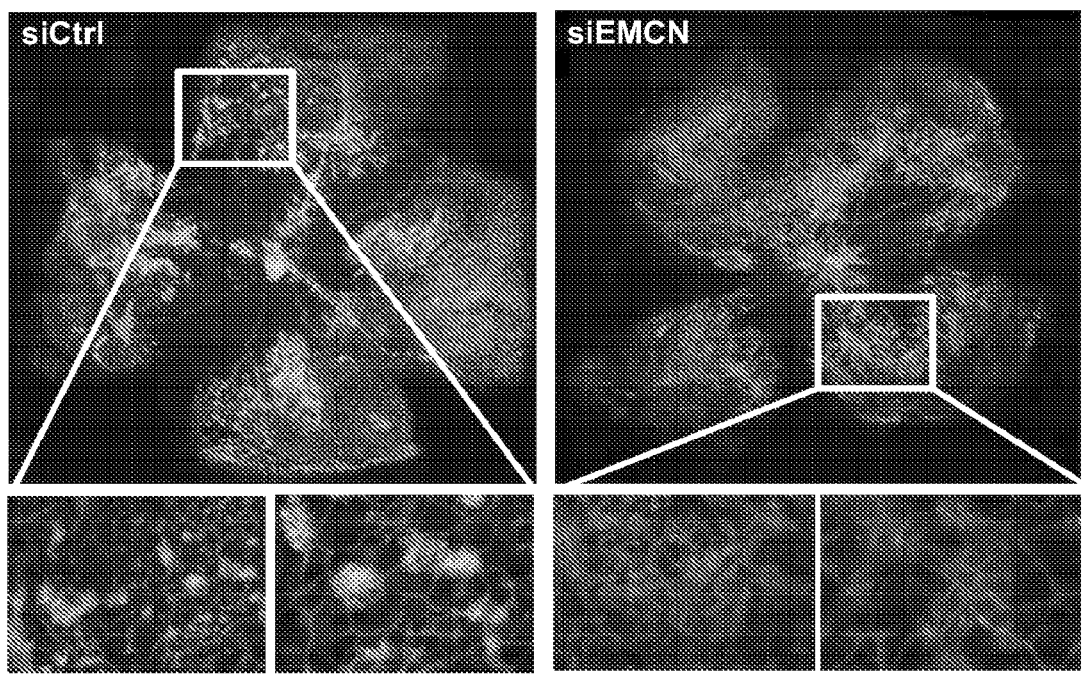
Figure 7B:
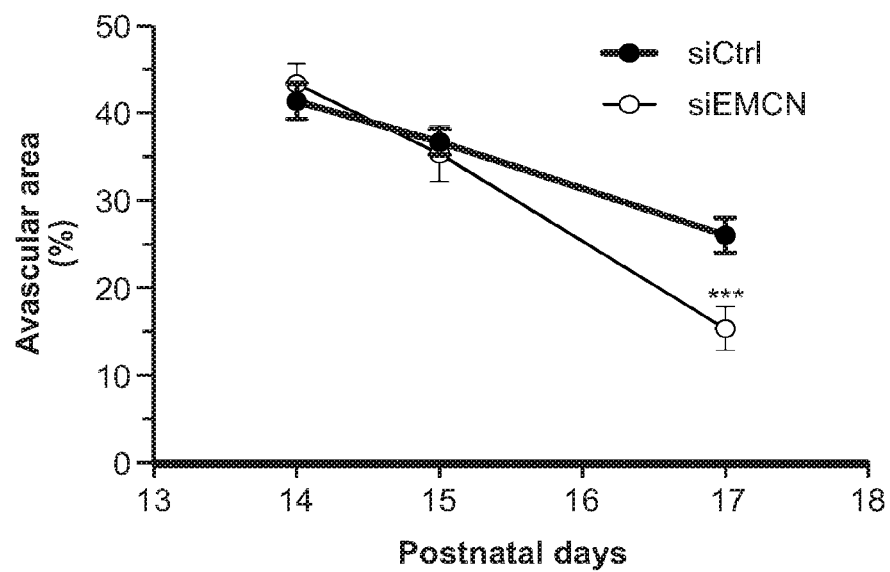

FIGS. 5A-5L show that inhibition or loss of EMCN results in defective retinal vascular development. P4 mice injected with siEMCN and scarified at P6 showed a reduced vascular plexus from the optic nerve head to the periphery indicative of impaired angiogenesis compared to siCtrl-injected mice (FIG. 5A, FIG. 5B and FIG. 5I). To further analyze the apparent impairment of angiogenesis caused by the knockdown of EMCN, vessel density (FIG. 5J), branch point number (FIG. 5K), and tip cell number (FIG. 5L) in P6 retinas were examined. All of these endpoints were significantly decreased in siEMCN-injected mice compared with littermate siRNA control injected mice. *P<0.05,  P<0.01, *P<0.001 siEMCN vs siCtrl. Error bars represent SEM. Scale bar 100 µm EMCN Controls Angiogenesis by Altering VEGFR2 Activation FIGS. 6A-6E demonstrate that EMCN controls angiogenesis by altering VEGFR2 activation. HRECs with or without siEMCN-mediated knockdown were stimulated with exogenous VEGF (10 ng/mL) and assessed for levels of VEGFR2 phosphorylation by immunoblot (FIG. 6A). FIG. 6B: VEGF treatment of cells with reduced EMCN displayed a 45% reduction in VEGFR2 phosphorylation compared to siCtrl cells. The level of phospho-VEGFR2 was also depressed in siEMCN treated cells compared to siCtrl cells in the absence of VEGF challenge. Examination of the effect of EMCN knockdown on the activation of ERK1/2 (FIG. 6C) and p38-MAPK (FIG. 6D) revealed a decrease in phospho-ERK1/2 and phospho-p38-MAPK expression in EMCN-deficient cells in response to VEGF treatment. FIG. 6E shows the results of a densitometry analysis and confirms reduced EMCN protein expression at all time points studied. *P<0.05, P<0.01, *P<0.001. Error bars represent SEM.

These results demonstrate that EMCN plays a central role in normal angiogenesis and reveals a novel function for EMCN in regulation of proangiogenic signaling in EC migration, proliferation, and morphogenesis and points to EMCN as an attractive target for treatment of angiogenesis-related diseases such as age-related macular degeneration, diabetic retinopathy, and many others.

Knockdown of EMCN

Knockdown or inhibition of EMCN has been demonstrated using RNA interferences, as described above. In addition to EMCN-specific siRNA, other strategies, e.g., gene editing, reducing gene expression such as Clustered Regularly Interspaced Short Palindromic Repeats (CRISPR)-based technologies, as well as transcription activator-like effector nucleases (TALENs)-based technologies EMCN inhibition as an anti-angiogenic therapy is distinguished from other known therapies such as anti-VEGF in that EMCN is expressed only by the endothelium and is upregulated during angiogenesis and thus represents a much more specific potential therapeutic target.

Anti-Angiogenic Agents to Reduce EMCN

The number of patients that will experience angiogenesis-related vision loss from pathologies such as diabetic eye disease, age-related macular degeneration, retinopathy of prematurity, and ischemic retinal vein occlusion is set to increase rapidly. Furthermore, though less prevalent than DR and AMD, retinopathy of prematurity (ROP) and ischemic retinal vein occlusion (IRVO) are also associated with pathologic angiogenesis and endothelial hyperpermeability in the retinal or choroidal vascular beds and lack effective treatment. The methods and compositions described herein are useful to treat such pathologies and are evaluated in art-recognized models, e.g., as described in Smith et al., 1994, Invest Ophthalmol Vis Sci., 35(1):101-111; Seo et al., 1999, Am. J. Path. 154 (6):1743-1753; and Grossnkklaus et al., 2010, Frog. Retin. Res. 29 (6): 500-519, each of which is hereby incorporated by reference.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for reducing neovascularization in an ocular tissue, comprising contacting said ocular tissue with an inhibitor of endomucin (EMCN) expression or activity, wherein said inhibitor comprises an EMCN-specific antibody or fragment thereof.

2. The method of claim 1, wherein said inhibitor reduces retinal neovascularization.

3. The method of claim 1, wherein said inhibitor reduces choroidal neovascularization.

4. The method of claim 1, wherein said ocular tissue comprises endothelial cells.

5. The method of claim 1, wherein said ocular tissue comprises vascular endothelial cells.

6. The method of claim 1, wherein said inhibitor is administered to a subject suffering from or at risk of developing age-related macular degeneration, diabetic retinopathy, retinopathy of prematurity, or ischemic retinal vein occlusion.

7. The method of claim 1, wherein said inhibitor is administered via injection.

8. The method of claim 1, wherein said inhibitor is administered topically.

9. The method of claim 6, wherein said subject is an infant.

10. The method of claim 6, wherein said subject is at least 50 years of age.

11. The method of claim 6, wherein said subject is at least 65 years of age.

12. The method of claim 1, wherein said method does not comprise administering said inhibitor to a heart, kidney, lung, or brain tissue.

13. The method of claim 1, wherein the EMCN-specific antibody or fragment thereof binds to an extracellular domain of EMCN.

14. The method of claim 13, wherein the extracellular domain of EMCN comprises residues 19-190 of SEQ ID NO: 2.

15. The method of claim 1, wherein binding of the EMCN-specific antibody or fragment thereof to EMCN reduces, inhibits, and/or blocks the binding of VEGF to VEGF-R.

16. The method of claim 1, wherein the EMCN-specific antibody or fragment thereof comprises at least one of polyclonal antibodies, monoclonal antibodies, chimeric antibodies, $F_v$, $F_{ab}$, $F_{ab'}$ and $F_{(ab')2}$ fragments, an Fab expression library, single-chain antibody molecules, multispecific antibodies, diabodies, linear antibodies, humanized antibodies, human antibodies and intrabodies.

17. The method of claim 16, wherein the EMCN-specific antibody or fragment thereof comprises at least one of antibodies of Cat Nos. LS-B10754 and LS-C201493 of LifeSpan BioSciences, antibodies of Cat Nos. PA5-21395, PA5-42745, and PA5-52229 of ThermoFisher Scientific, and antibodies of Cat Nos. ABIN2782254, ABIN1385912, ABIN2157259 of Antibodies-online.

18. A method for treating aberrant or pathological angiogenesis in an ocular tissue of a subject, comprising diagnosing a subject with aberrant or pathological angiogenesis in an ocular tissue and contacting said ocular tissue with an inhibitor of endomucin (EMCN) expression or activity, wherein said inhibitor comprises an EMCN-specific antibody or fragment thereof.

* * * * *

SEQUENCE LISTING

<160> NUMBER OF SEQ ID NOS: 7

<210> SEQ ID NO 1
<211> LENGTH: 19
<212> TYPE: RNA
<213> ORGANISM: Artificial Sequence
<220> FEATURE:
<223> OTHER INFORMATION: siRNA sequence

<400> SEQUENCE: 1
ugguuuacau gucgacuaa                                        19

<210> SEQ ID NO 2
<211> LENGTH: 261
<212> TYPE: PRT
<213> ORGANISM: Homo sapiens

<400> SEQUENCE: 2

```
Met Glu Leu Leu Gln Val Thr Ile Leu Phe Leu Leu Pro Ser Ile Cys
1               5                   10                  15

Ser Ser Asn Ser Thr Gly Val Leu Glu Ala Ala Asn Asn Ser Leu Val
            20                  25                  30

Val Thr Thr Thr Lys Pro Ser Ile Thr Thr Pro Asn Thr Glu Ser Leu
        35                  40                  45

Gln Lys Asn Val Val Thr Pro Thr Thr Gly Thr Thr Pro Lys Gly Thr
    50                  55                  60

Ile Thr Asn Glu Leu Leu Lys Met Ser Leu Met Ser Thr Ala Thr Phe
65                  70                  75                  80

Leu Thr Ser Lys Asp Glu Gly Leu Lys Ala Thr Thr Asp Val Arg
                85                  90                  95

Lys Asn Asp Ser Ile Ile Ser Asn Val Thr Val Thr Ser Val Thr Leu
                100                 105                 110

Pro Asn Ala Val Ser Thr Leu Gln Ser Ser Lys Pro Lys Thr Glu Thr
            115                 120                 125

Gln Ser Ser Ile Lys Thr Thr Glu Ile Pro Gly Ser Val Leu Gln Pro
    130                 135                 140

Asp Ala Ser Pro Ser Lys Thr Gly Thr Leu Thr Ser Ile Pro Val Thr
145                 150                 155                 160

Ile Pro Glu Asn Thr Ser Gln Ser Gln Val Ile Gly Thr Glu Gly Gly
                165                 170                 175

Lys Asn Ala Ser Thr Ser Ala Thr Ser Arg Ser Tyr Ser Ser Ile Ile
            180                 185                 190

Leu Pro Val Val Ile Ala Leu Ile Val Ile Thr Leu Ser Val Phe Val
        195                 200                 205

Leu Val Gly Leu Tyr Arg Met Cys Trp Lys Ala Asp Pro Gly Thr Pro
    210                 215                 220

Glu Asn Gly Asn Asp Gln Pro Gln Ser Asp Lys Glu Ser Val Lys Leu
225                 230                 235                 240

Leu Thr Val Lys Thr Ile Ser His Glu Ser Gly Glu His Ser Ala Gln
                245                 250                 255

Gly Lys Thr Lys Asn
                260
```

<210> SEQ ID NO 3
<211> LENGTH: 4047
<212> TYPE: DNA
<213> ORGANISM: Homo sapiens

<400> SEQUENCE: 3

```
gggagtgtgt gtatttcctc ccgttcttta tcagagcccc caaataagt aggaatgggc      60 agtggctatt cacattcact acacctttc catttgctaa taaggccctg ccaggctggg     120
agggaattgt ccctgcctgc ttctggagaa agaagatatt gacaccatct acgggcacca    180
tggaactgct tcaagtgacc attcttttc ttctgcccag tatttgcagc agtaacagca    240
caggtgtttt agaggcagct aataattcac ttgttgttac tacaacaaaa ccatctataa    300
caacaccaaa cacagaatca ttacagaaaa atgttgtcac accaacaact ggaacaactc    360
ctaaaggaac aatcaccaat gaattactta aatgtctct gatgtcaaca gctactttt    420 taacaagtaa agatgaagga ttgaaagcca aaccactga tgtcaggaag aatgactcca    480
tcatttcaaa cgtaacagta acaagtgtta cacttccaaa tgctgtttca acattacaaa    540
```

```
gttccaaacc caagactgaa actcagagtt caattaaaac aacagaaata ccaggtagtg      600
ttctacaacc agatgcatca ccttctaaaa ctggtacatt aacctcaata ccagttacaa      660
ttccagaaaa cacctcacag tctcaagtaa taggcactga gggtggaaaa aatgcaagca      720
cttcagcaac cagccggtct tattccagta ttattttgcc ggtggttatt gctttgattg      780
taataacact ttcagtattt gttctggtgg gtttgtaccg aatgtgctgg aaggcagatc      840
cgggcacacc agaaaatgga aatgatcaac ctcagtctga taaagagagc gtgaagcttc      900
ttaccgttaa gacaatttct catgagtctg gtgagcactc tgcacaagga aaaaccaaga      960
actgacagct tgaggaattc tctccacacc taggcaataa ttacgcttaa tcttcagctt     1020
ctatgcacca agcgtggaaa aggagaaagt cctgcagaat caatcccgac ttccatacct     1080
gctgctggac tgtaccagac gtctgtccca gtaaagtgat gtccagctga catgcaataa     1140
tttgatggaa tcaaaagaa ccccgggct ctcctgttct ctcacattta aaaattccat     1200
tactccattt acaggagcgt tcctaggaaa aggaatttta ggaggagaat tgtgagcag     1260 tgaatctgac agcccaggag gtgggctcgc tgataggcat gactttcctt aatgtttaaa     1320
gttttccggg ccaagaattt ttatccatga agactttcct acttttctca gtgttcttat     1380
attacctact gttagtattt attgtttacc actatgttaa tgcagggaaa agttgcacgt     1440
gtattattaa atattaggta gaaatcatac catgctactt tgtacatata agtattttat     1500
tcctgctttc gtgttacttt taataaataa ctactgtact caatactcta aaaatactat     1560
aacatgactg tgaaaatggc aatgttattg tcttcctata attatgaata ttttttggatg    1620 gattattaga atacatgaac tcactaatga aaggcatttg taataagtca gaaagggaca     1680
tacgattcac atatcagact gttaggggga gagtaattta tcagttcttt ggtcttccta     1740
tttgtcattc atactatgtg atgaagatgt aagtgcaagg gcatttataa cactatactg     1800
cattcattaa gataataggs tcatgatttt tcattaactc atttgattga tattatctcc     1860
atgcattttt tattctttt agaaatgtaa ttatttgctc tagcaatcat tgctaacctc     1920 tagttttgtag aaaatcaaca ctttataaat acataattat gatattattt ttcattgtat     1980
cactgttcta aaaataccat atgattatag ctgccactcc atcaggagca aattcttctg     2040
ttaaaagcta actgatcaac cttgaccact ttttgacat gtgagatcaa agtgtcaagt     2100
tggctgaggt ttttttggaaa gctttagaac taataagctg ctggtggcag ctttgtaacg     2160
tatgattatc taagctgatt ttgatgctaa attatcttag tgatctaagg ggcagtttag     2220
tgaagatgga atcttgtatt taaaatagcc ttttaaaatt tgttttgtgg tgatgtattt     2280
tgacaacttc catctttagg agtatataa tcaccttgat tttagtttcc tgatgtttgg     2340
actatttata atcaaggaca ccaagcaagc ataagcatat ctatatttct gactggtgtc     2400 tcttttgagaa ggatgggaag tagaaaaaaa aaaagaaag aaggaaagg aagagaggag     2460 agaagaaggc agggatctcc actatgtatg ttttcacttt agaactgttg agcccatgct     2520 taatttaat ctagaagtct ttaaatggtg agacagtgac tggagcatgc caatcagaga     2580
gcatttgtct tcagaaaaa aaaaaatctg agtttgagac tagcctggcc aacatgttga     2640
aaccccatat ctactaaaa tacaaaaatt agcctggtgt ggtggcgcac gcctgtagtc     2700
ccagctactc tggagcctga ggaacgtgaa tcgcttgaac ccagaagaca gaggttgcag     2760
tgagctgaga tggcactatt gcactccagc ctgggtgaca cagcaagact ctgtctcaaa     2820
aaaaaaaaaa aaaaaagga aaaaaagaa agaaagaaag tcccagcaca cctagataat     2880
```

-continued

| | |
|---|---|
| ttaccgagct cttcagcaaa aaccatgtta catacagcat attccaaaga aatgaactct | 2940 |
| tctgcaattt aaattataag taatatgtta ttttggatcc tagagaaacc attttctcta | 3000 |
| catttcatga gcatggttag aaaagagttt acaagaatta ggaagaggga acaattttaa | 3060 |
| tggtcagaaa agaataaaat ttattctagt tcaagaagtg cacacaaaga atatgcatta | 3120 |
| atctaacaac tatgagatta aatctttcaa aaaggtcaaa ggaggattga aagtttaca | 3180 |
| gagatgtcca cggcatttta tatcaatctc aaaggtaagg tctgcatttt tataaaccaa | 3240 |
| cttaaacttc tgttgagata ggatattttg ttttcaagcc aaaattacca ttaatcaaat | 3300 |
| atgttttaat tatctgattt agatgatcta cttttatgc ctggcttact gtaagttttt | 3360 |
| tattctgata cacagttcaa acatcattgc aacaaagaag tgcctgtatt tagatcaaag | 3420 |
| gcaagacttt ctatgtgttt gttttgcata ataatatgaa tataatttaa gtctatcaat | 3480 |
| agtcaaaaca taaacaaaag ctaattaact ggcactgttg tcacctgaga ctaagtggat | 3540 |
| gttgttggct gacatacagg ctcagccagc agagaaagaa ttctgaattc cccttgctga | 3600 |
| actgaactat tctgttacat atggttgaca aatctgtgtg ttatttcttt tctacctacc | 3660 |
| atatttaaat ttatgagtat caaccgagga catagtcaaa ccttcgatga tgaacattcc | 3720 |
| tgatttttg cctgattatt ctctgttgag ctctacttgt ggtcattcaa gatttttatga | 3780 |
| tgttgaaagg aaaagtgaat atgaccttta aaaattgtat tttgggtgat gatagtctca | 3840 |
| ccactataaa actgtcaatt attgcctaat gttaaagata tccatcattg tgattaatta | 3900 |
| aacctataat gagtattctt aatggagaat tcttaatgga tggattatcc cctgatcttt | 3960 |
| tctttaaaat ttctctgcac acacaggact tctcattttc caataaatgg gtgtactctg | 4020 |
| ccccaatttc tagggaaaaa aaaaaaa | 4047 |

```
<210> SEQ ID NO 4
<211> LENGTH: 19
<212> TYPE: RNA
<213> ORGANISM: Artificial Sequence
<220> FEATURE:
<223> OTHER INFORMATION: siRNA sequence

<400> SEQUENCE: 4
gcgugaagcu ucuuaccgu                                               19

<210> SEQ ID NO 5
<211> LENGTH: 19
<212> TYPE: RNA
<213> ORGANISM: Artificial Sequence
<220> FEATURE:
<223> OTHER INFORMATION: siRNA sequence

<400> SEQUENCE: 5
aggcaauaau uacgcuuaa                                               19

<210> SEQ ID NO 6
<211> LENGTH: 19
<212> TYPE: RNA
<213> ORGANISM: Artificial Sequence
<220> FEATURE:
<223> OTHER INFORMATION: siRNA sequence

<400> SEQUENCE: 6
ggaaaaguug cacguguau                                               19

<210> SEQ ID NO 7
<211> LENGTH: 19
```

```
<212> TYPE: RNA
<213> ORGANISM: Artificial Sequence
<220> FEATURE:
<223> OTHER INFORMATION: siRNA sequence

<400> SEQUENCE: 7
caucauuuca aacguaaca                                                 19
```